(12) United States Patent
Bhowmick et al.

(10) Patent No.: US 11,583,292 B2
(45) Date of Patent: Feb. 21, 2023

(54) DEVICES AND METHODS FOR TREATMENT OF HEMORRHOIDS

(71) Applicant: BOSTON SCIENTIFIC LIMITED, Hamilton (BM)

(72) Inventors: Nabarun Bhowmick, Kolkata (IN); Deepak Kumar Sharma, Muzaffarnafar (IN); Charudatta Chandrakant Aradhye, Solapur (IN); Rohit Rohilla, Rohtak (IN); Agrim Mishra, New Dehli (IN); Balaji Aswatha Narayana, Bangalore (IN); Nidhi Dhingra, Ludhiana (IN); Abhishek Basu, Gurgaon (IN); Hitendra Purohit, Vadodara (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 359 days.

(21) Appl. No.: 16/922,841

(22) Filed: Jul. 7, 2020

(65) Prior Publication Data

US 2021/0030424 A1 Feb. 4, 2021

Related U.S. Application Data

(60) Provisional application No. 62/879,841, filed on Jul. 29, 2019.

(51) Int. Cl.
*A61B 17/128* (2006.01)
*A61B 1/31* (2006.01)
(Continued)

(52) U.S. Cl.
CPC ............ *A61B 17/1285* (2013.01); *A61B 1/31* (2013.01); *A61B 1/32* (2013.01); *A61B 2017/00818* (2013.01)

(58) Field of Classification Search
CPC ........... A61B 1/31; A61B 1/32; A61B 17/128; A61B 17/1285; A61B 2017/00818; A61B 2017/3452
See application file for complete search history.

(56) References Cited

U.S. PATENT DOCUMENTS 2,922,415 A * 1/1960 Campagna ............... A61B 1/31
600/184
5,158,563 A 10/1992 Cosman
(Continued)

FOREIGN PATENT DOCUMENTS

AU 2012244280 11/2012
CN 105943100 9/2016
(Continued)

*Primary Examiner* — Ryan J. Severson
(74) *Attorney, Agent, or Firm* — Fay Kaplun & Marcin, LLP

(57) ABSTRACT

A device includes an anoscope including an elongated hollow member with a longitudinal slot configured to receive tissue in an interior of the hollow member. The device also includes a clip applicator. The clip applicator includes a body slidably received in the slot and jaws at a distal end of the body configured to hold a ligation clip. The clip applicator further includes a plunger slidably coupled to the body configured to actuate the jaws. When the clip applicator is inserted into the slot and the plunger is moved relative to the body, the jaws close and deform the ligation clip from an open position into a closed position around tissue received in the slot.

20 Claims, 21 Drawing Sheets

(51) Int. Cl.
*A61B 1/32* (2006.01)
*A61B 17/00* (2006.01)

(56) References Cited

U.S. PATENT DOCUMENTS

| | | | |
|---|---|---|---|
| 6,126,594 A | 10/2000 | Bayer | |
| 6,142,931 A * | 11/2000 | Kaji | A61B 17/3421 600/105 |
| 7,037,314 B2 | 5/2006 | Armstrong | |
| 8,097,002 B2 | 1/2012 | Delaney | |
| 8,292,904 B2 * | 10/2012 | Popovic | A61B 17/072 606/142 |
| 9,044,213 B1 * | 6/2015 | Lonky | A61B 10/0291 |
| 9,232,947 B2 | 1/2016 | Brenner et al. | |
| 9,307,896 B2 | 4/2016 | Rebuffat et al. | |
| 9,795,367 B1 * | 10/2017 | Lee | A61B 1/32 |
| 9,867,633 B2 | 1/2018 | Piskun | |
| 10,959,730 B2 * | 3/2021 | Lee | A61B 17/083 |
| 2002/0111639 A1 * | 8/2002 | Armstrong | A61B 1/31 606/144 |
| 2003/0233142 A1 * | 12/2003 | Morales | A61B 8/12 623/2.37 |
| 2006/0009797 A1 | 1/2006 | Armstrong | |
| 2006/0264706 A1 * | 11/2006 | Piskun | A61B 17/22 600/105 |
| 2008/0243145 A1 * | 10/2008 | Whitfield | A61B 90/08 606/143 |
| 2008/0262511 A1 | 10/2008 | Delaney | |
| 2010/0023023 A1 * | 1/2010 | Popovic | A61B 17/068 606/151 |
| 2012/0059394 A1 * | 3/2012 | Brenner | A61B 17/122 606/142 |
| 2014/0100423 A1 | 4/2014 | Monassevitch et al. | |
| 2016/0106435 A1 * | 4/2016 | Brenner | A61B 1/31 600/439 |
| 2019/0142426 A1 * | 5/2019 | Lee | A61B 17/083 606/142 |
| 2021/0015354 A1 * | 1/2021 | Windheuser | A61B 1/015 |
| 2021/0022746 A1 * | 1/2021 | Smith | A61B 17/32056 |
| 2021/0030424 A1 * | 2/2021 | Bhowmick | A61B 1/31 |

FOREIGN PATENT DOCUMENTS

| | | |
|---|---|---|
| CN | 206080487 | 4/2017 |
| WO | 01/43626 | 6/2001 |
| WO | 2007/093198 | 8/2007 |
| WO | 2010/096174 | 8/2010 |
| WO | 2017/172835 | 10/2017 |

* cited by examiner

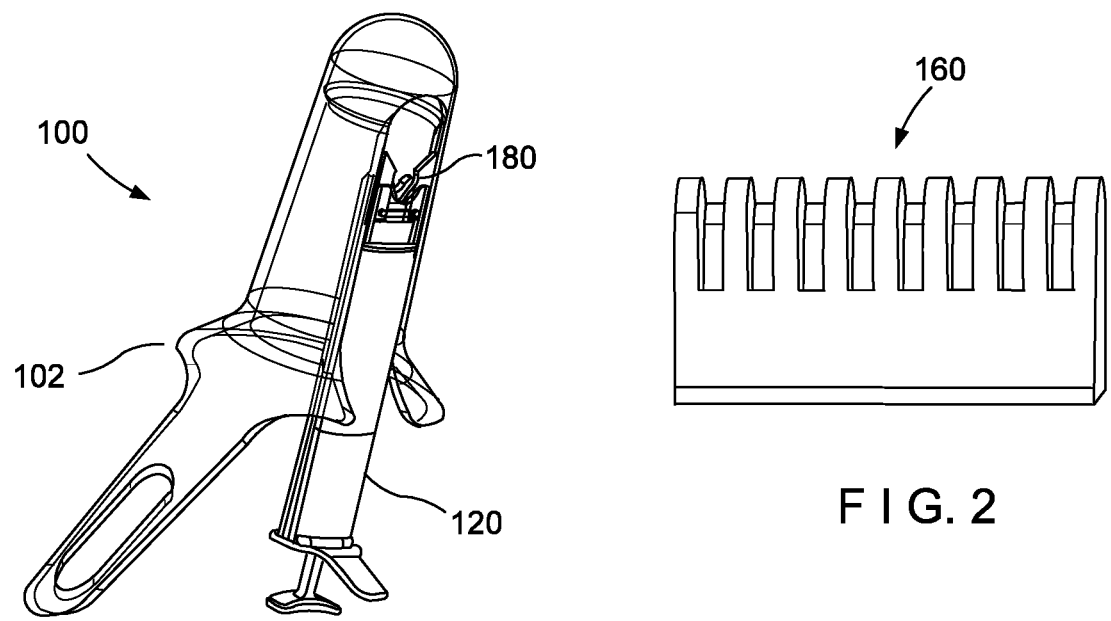
F I G. 1
F I G. 2
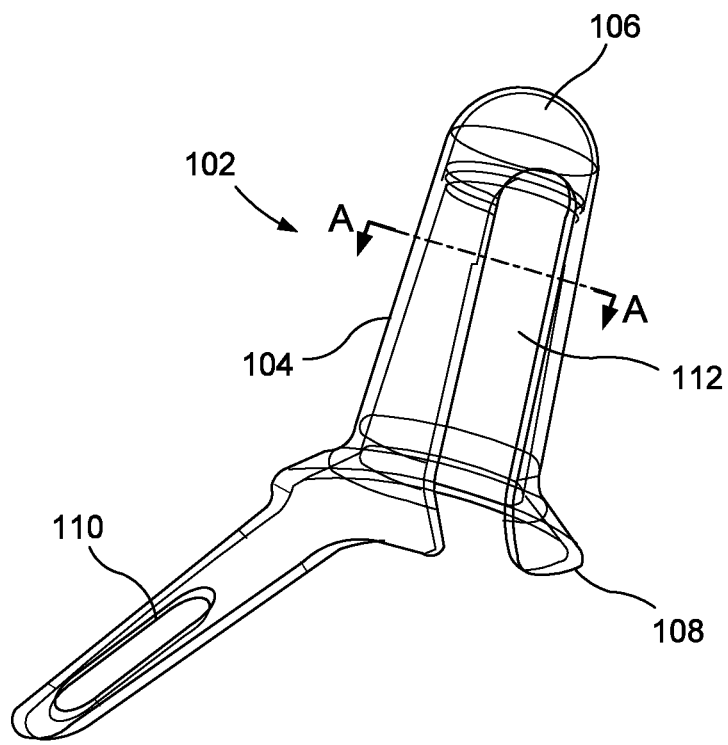
F I G. 3

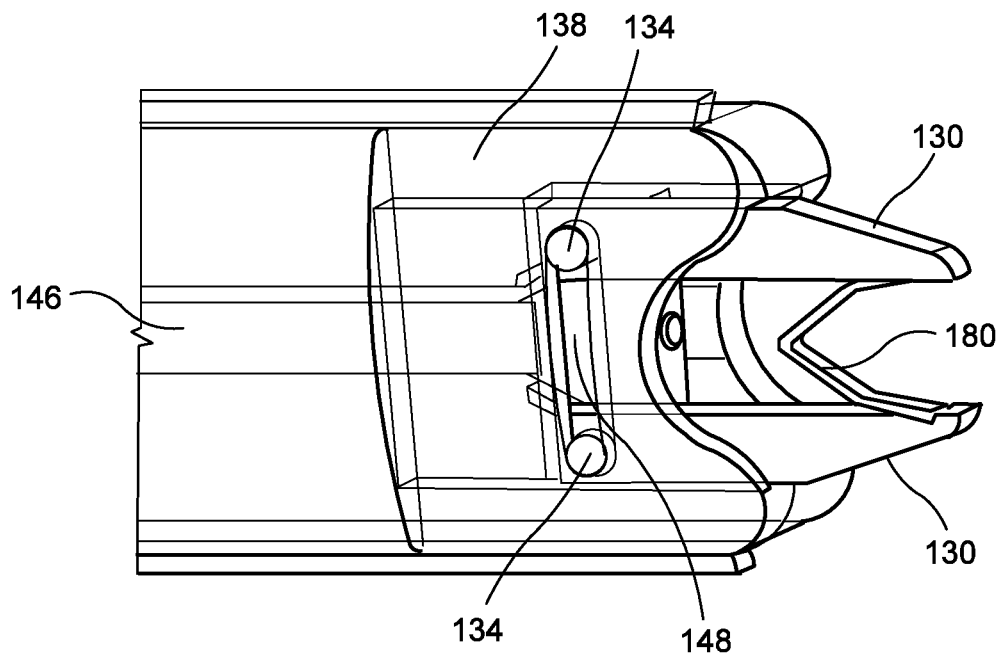
F I G. 13A
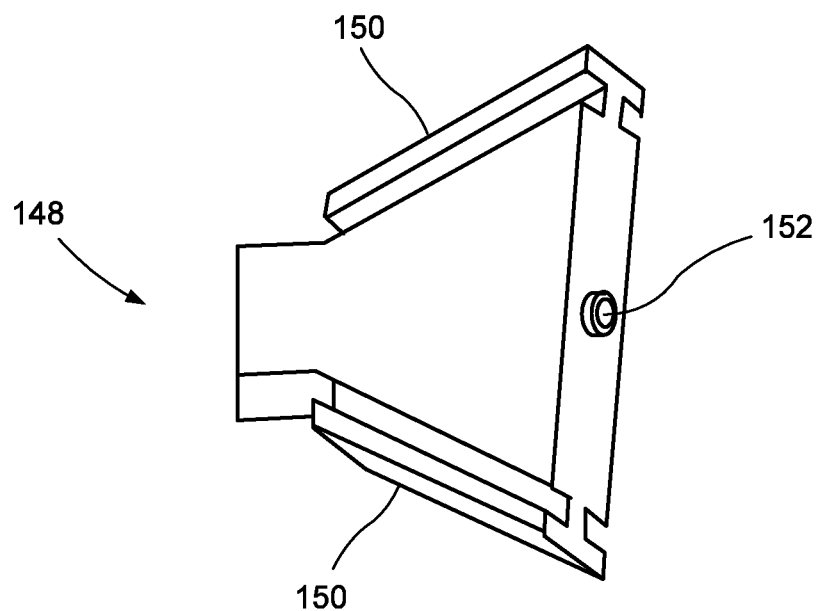
F I G. 14

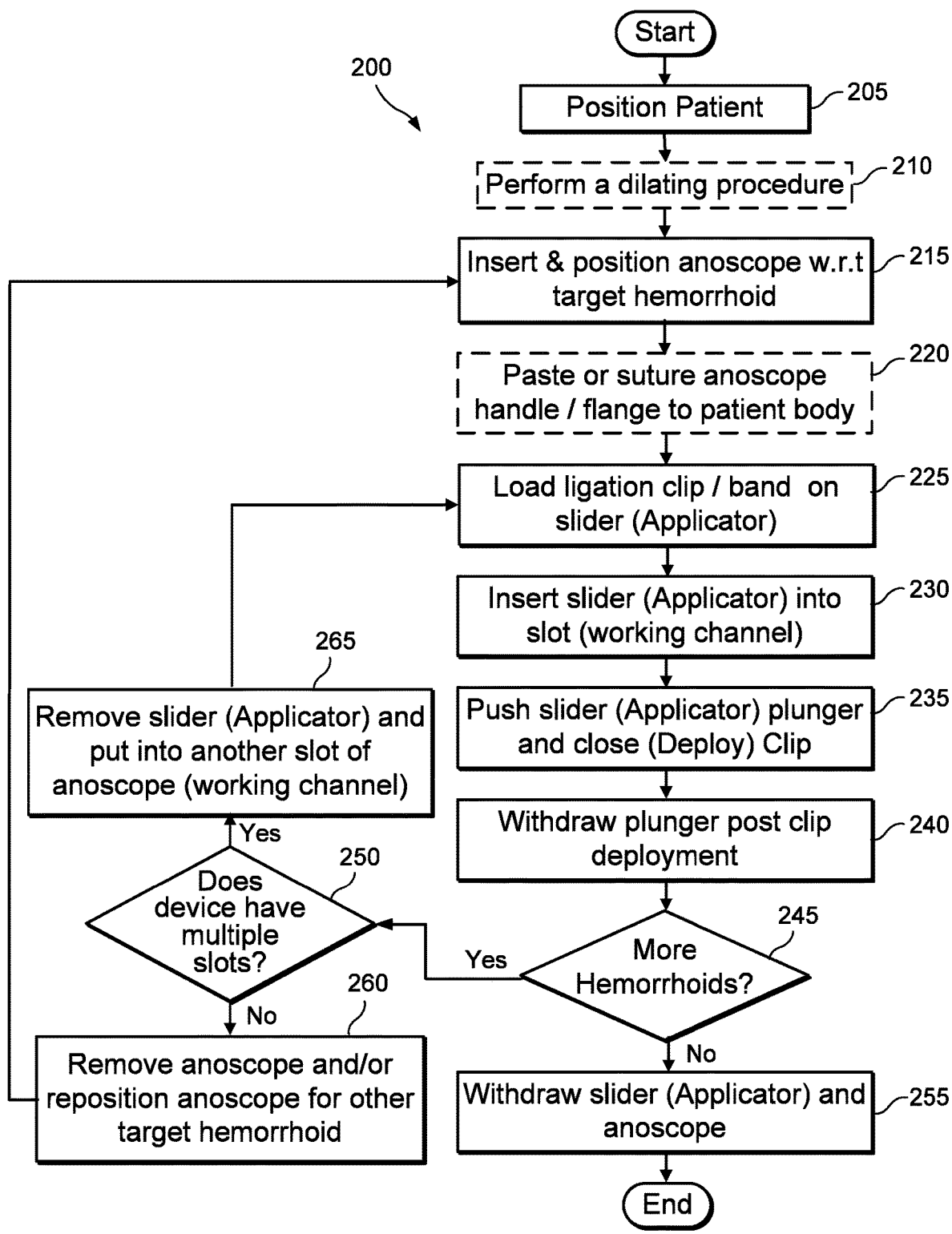
F I G. 20

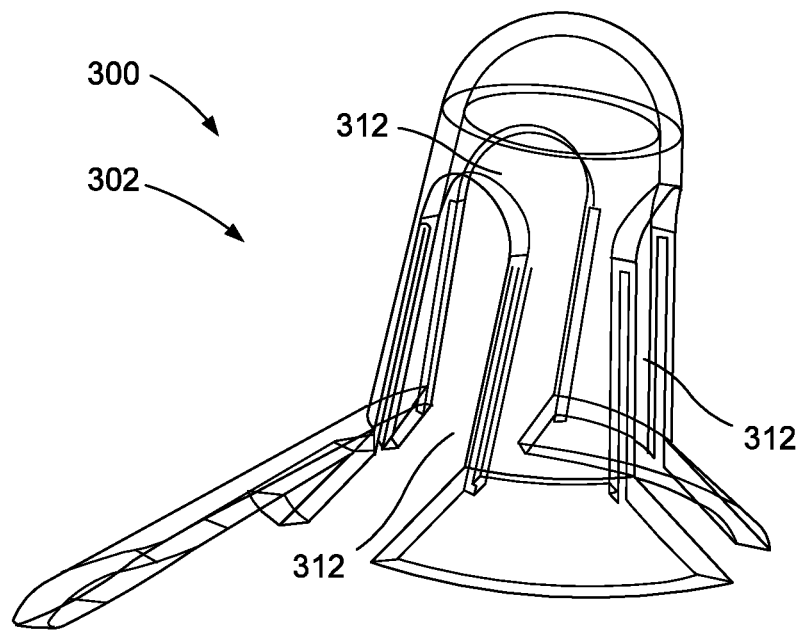
F I G. 22
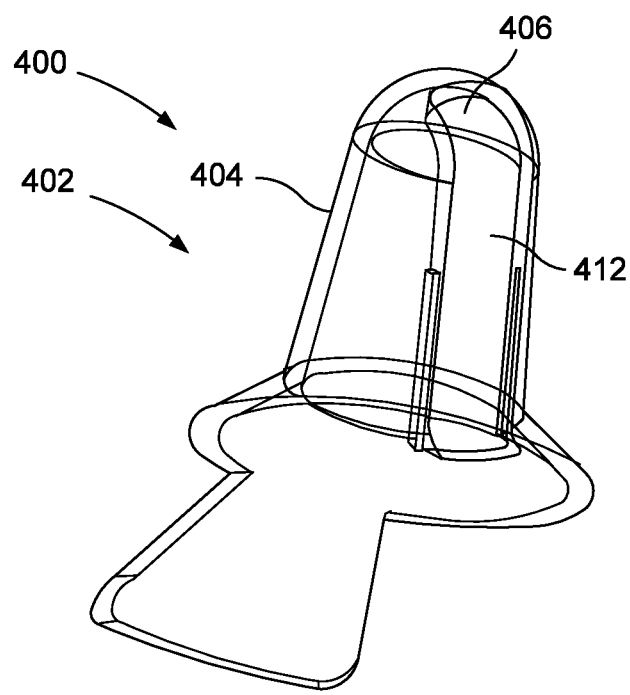
F I G. 23

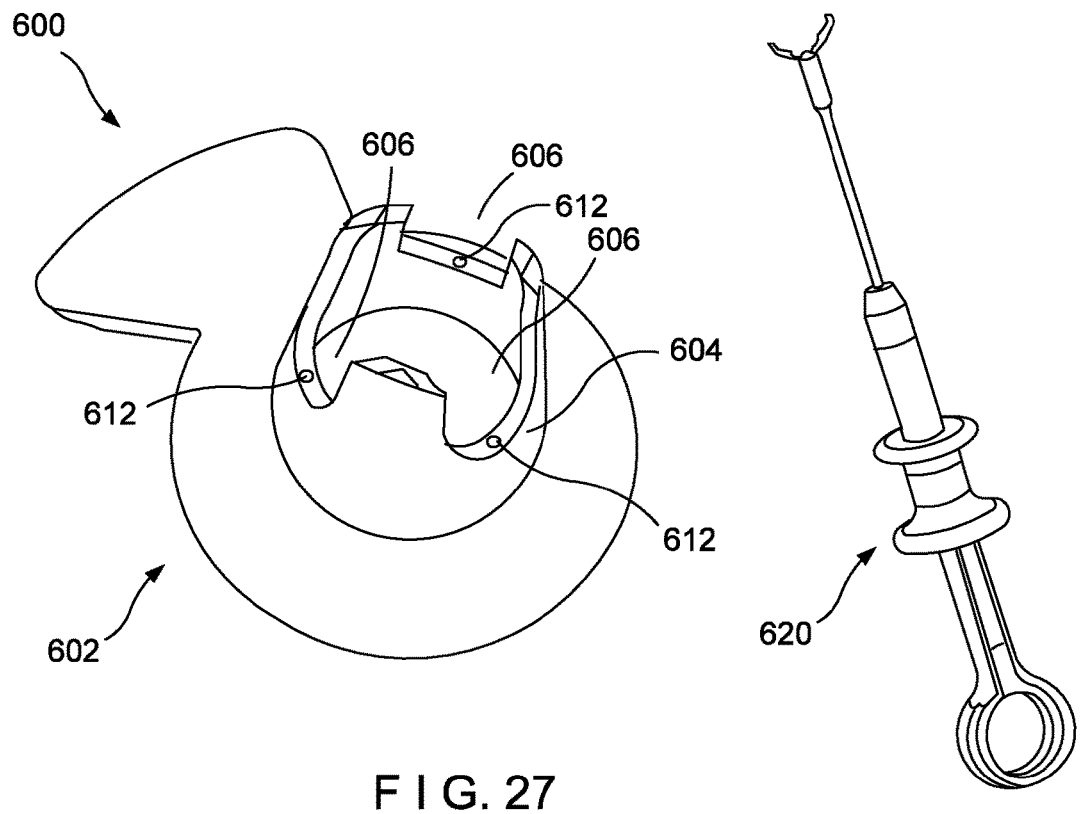
FIG. 27
FIG. 28
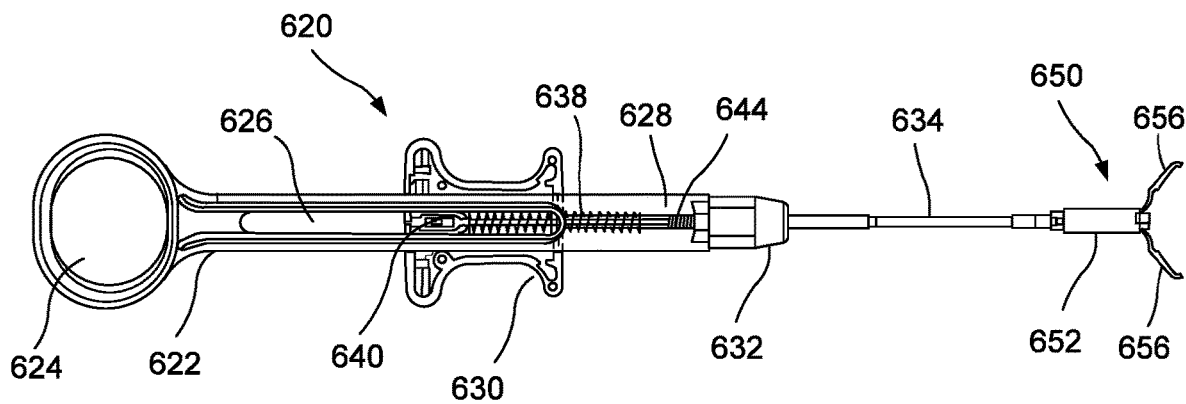
FIG. 29

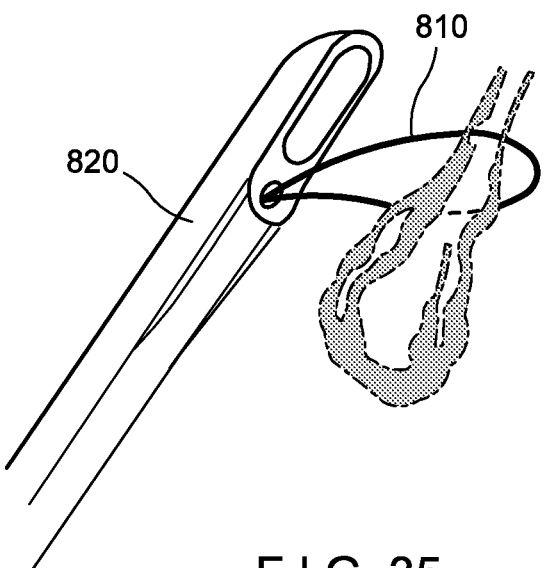
F I G. 35
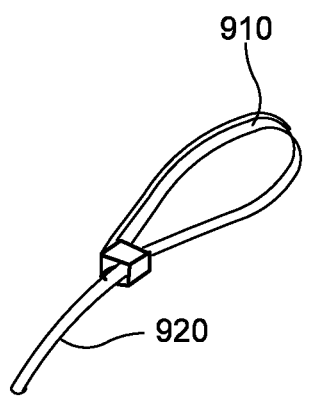
F I G. 36A
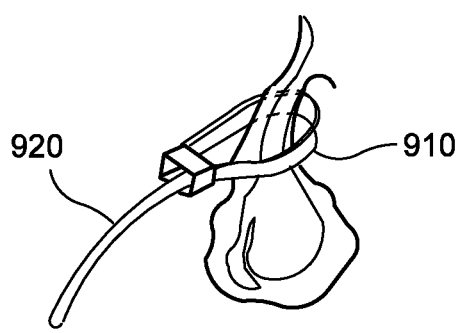
F I G. 36B
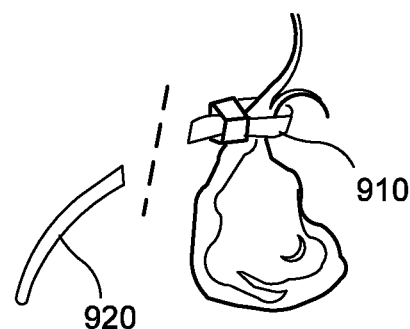
F I G. 36C

DEVICES AND METHODS FOR TREATMENT OF HEMORRHOIDS

PRIORITY CLAIM

The present disclosure claims priority to U.S. Provisional Patent Application Ser. No. 62/879,841 filed Jul. 29, 2019; the disclosure of which is incorporated herewith by reference.

FIELD

The present disclosure relates to a device and a method for treatment of hemorrhoids. In particular, the present disclosure relates to devices and methods to access a root of hemorrhoid and treat multiple internal hemorrhoids.

BACKGROUND

Hemorrhoids are swollen and inflamed veins around the anus or in the lower rectum. Hemorrhoids may be external, forming under the skin around the anus, or internal, forming in the lining of the anus and the lower rectum. Ligation is a common method for treating hemorrhoids. A band or clip is placed at the base of the hemorrhoid strangulating blood flow thereto, reducing inflammation and eventually eliminating the hemorrhoid. The clips may be metal and deformable such that closing the clip about the base of the hemorrhoid will deform the clip into a closed, crimped shape.

SUMMARY

The present disclosure relates to a device which includes an anoscope including an elongated hollow member with a longitudinal slot configured to receive tissue in an interior of the hollow member; and a clip applicator. The clip application includes a body slidably received in the slot and jaws at a distal end of the body configured to hold a ligation clip. The clip applicator further includes a plunger slidably coupled to the body configured to actuate the jaws. When the clip applicator is inserted into the slot and the plunger is moved relative to the body, the jaws close and deform the ligation clip from an open position into a closed position around tissue received in the slot.

In an embodiment, the clip applicator includes a slider unit and the device further includes rails extending along a longitudinal side of the slider unit, each of the rails being sized and shaped to be inserted through a corresponding channel extending along at least a portion of a longitudinal edge of a corresponding one of the slots.

In an embodiment, the device further includes a notch at a distal end of each of the jaws, each of the notches abutting an end of the ligation clip to hold and lock the clip in a configuration; and a pin at a proximal end of each of the jaws, each of the pins maintaining parallel and simultaneous movement between the jaws.

In an embodiment, the device further includes a linkage constructed to facilitate movement of the jaws from the open position to the closed position when the plunger is pushed proximally towards the body of the slider unit until the plunger abuts the proximal end of the body of the slider unit.

In an embodiment, the linkage includes a pair of angled slots at a distal end of the plunger, each of the angled slots being sized and shaped to receive a rib extending radially inward from each of the jaws.

In an embodiment, the device further includes a clip cartridge housing a plurality of ligation bands.

In an embodiment, the jaws are locked in a proximal direction and a distal direction, restricting the jaws to lateral movement, transverse to a longitudinal axis of the clip applicator.

In an embodiment, the clip applicator further includes a handle portion extending from a proximal end to a distal end; a thumb ring attached to the proximal end; a longitudinal slot extending a portion of a length of the handle distal to the thumb ring; a core wire; a spool disposed around the handle, the spool slidable between the proximal end and the distal end of the longitudinal slot; and a thin flexible coil extending distally from the distal end of the handle.

In an embodiment, the spool is a spring-biased with respect to the handle.

In an embodiment, the clip assembly further includes a capsule extending from a proximal end to a distal end and housing a yoke slidable therewithin; and two clip jaws, sized and shaped to grasp tissue, the jaws extending through two holes at the distal end of the capsule, attached to the yoke.

In an embodiment, the clip applicator further comprising a feedback notification notifying a user when the clip is deployed.

In an embodiment, the feedback notification is one of an aural feedback or a tactile feedback.

In an embodiment, the anoscope further includes a distal tip with a curved surface for insertion into an anal cavity.

The present disclosure also relates to a system which includes a dilator sized and shaped for insertion into an anal cavity; and a device. The device includes an anoscope including an elongated hollow member with a longitudinal slot configured to receive tissue in an interior of the hollow member; and a clip applicator including a body slidably received in the slot. The clip applicator includes jaws at a distal end of the body configured to hold a ligation clip. The clip applicator further includes a plunger slidably coupled to the body configured to actuate the jaws. When the clip applicator is inserted into the slot and the plunger is moved relative to the body, the jaws close and deform the ligation clip from an open position into a closed position around tissue received in the slot. The dilator is configured to be inserted into the anal cavity prior to the insertion of the anoscope into the anal cavity.

In an embodiment, the anoscope is insertable into the anal cavity via the dilator.

The present disclosure further relates to a method including inserting an anoscope into an anal cavity, the anoscope including an elongated hollow member with a longitudinal slot for receiving tissue in an interior of the hollow member; inserting a clip applicator through the slot to engage target tissue, the clip applicator including a body slidably received in the slot, the clip applicator including jaws at a distal end of the body for holding a ligation clip, the clip applicator further including a plunger slidably coupled to the body for actuating the jaws; positioning the clip applicator so that a first target portion of tissue is received between the jaws; and moving the plunger relative to the body to close the jaws and deform the ligation clip from an open position into a closed position around the first target portion of tissue received between the jaws.

In an embodiment, the method further includes withdrawing the plunger relative to the body to open the jaws; removing the clip applicator through the slot and out of the anal cavity; repositioning the anoscope to receive a second target portion of tissue into the slot; inserting the clip applicator into the slot; and moving the plunger relative to the body to close the jaws and deform the ligation clip from the open position into the closed position around the second target portion of tissue received in the slot.

In addition, the present disclosure relates to a device which includes an anoscope including an elongated hollow member with an open distal end configured to receive tissue in an interior of the hollow member and at least one longitudinal channel; and a clip applicator including a distal portion slidably received in the channel. The clip applicator includes jaws at a distal end of the body configured to hold a ligation clip. The clip applicator further includes a plunger slidably coupled to the body configured to actuate the jaws. When the clip applicator is inserted into the channel and the plunger is moved relative to the body, the jaws close and deform the ligation clip from an open position into a closed position around tissue received in the open distal end.

Furthermore, the present disclosure relates to a method which includes inserting an anoscope into an anal cavity, the anoscope including an elongated hollow member with an open distal end for receiving tissue in an interior of the hollow member and a plurality of longitudinal channels; inserting a clip applicator into a first one of the channels, the clip applicator including a distal portion slidably received in the first channel, the clip applicator including jaws at a distal end of the body for holding a ligation clip, the clip applicator further including a plunger slidably coupled to the body for actuating the jaws; and moving the plunger relative to the body to close the jaws and deform the ligation clip from an open position into a closed position around a first target portion of tissue received in the open distal end.

In an embodiment, the method further includes withdrawing the plunger relative to the body to open the jaws; removing the clip applicator from the first channel; inserting the clip applicator into a second one of the channels; and moving the plunger relative to the body to close the jaws and deform the ligation clip from the open position into the closed position around a second target portion of tissue received in the open distal end.

BRIEF DESCRIPTION

FIG. 1 shows a ligation device according to a first exemplary embodiment including an anoscope and a slider unit for applying a ligation clip to a hemorrhoid.

FIG. 2 shows a clip cartridge holding a plurality of ligation clips for loading the slider unit of FIG. 1.

FIG. 3 shows a perspective view of the anoscope of FIG. 1 without the slider unit.

FIG. 13A shows a transparent view of a distal end of the slider unit of FIG. 5.

FIG. 14 shows a distal head of a plunger of the slider unit of FIG. 5.

FIG. 20 shows a method for performing a ligation procedure.

FIG. 22 shows a device comprising an anoscope according to a second exemplary embodiment.

FIG. 23 shows a device comprising an anoscope according to a third exemplary embodiment.

FIG. 27 shows views of a device comprising an anoscope according to a fifth exemplary embodiment.

FIG. 28 shows a perspective view of a clip applicator for use with the anoscope of FIG. 27.

FIG. 29 shows a transparent top view of a clip applicator for use with the anoscope of FIG. 27.

FIG. 35 shows an electrocautery loop for use with an anoscope.

FIG. 36A shows views of an adjustable band for use with an anoscope.

FIG. 36B shows a view of the adjustable band of FIG. 36A adjusting around the hemorrhoid.

FIG. 36C shows a view of the adjustable band of FIG. 36A tightened around the hemorrhoid.

DETAILED DESCRIPTION

Figure 4:
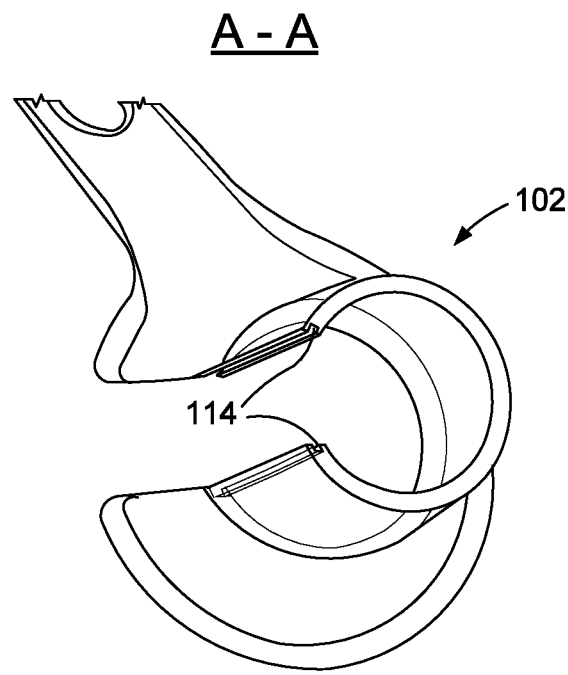
FIG. 4 shows a perspective cut view along line A-A of a slot in the anoscope of FIG. 3 for receiving the slider unit.

The present disclosure may be further understood with reference to the following description and the appended drawings, wherein like elements are referred to with the same reference numerals. Commercially available anoscopes allow physicians to visualize and access the anal cavity while treating a patient. It is desirable to have a combined device for visualizing, accessing and treating hemorrhoids. The present disclosure is directed to a device including an anoscope and a clip applicator for ligating one or more hemorrhoids. The exemplary device may access the anal cavity, visualize a hemorrhoidal treatment area, and crimp a ligation band/clip around the base/root of the one or more hemorrhoids. It is noted that the terms proximal and distal, as used herein, refer to a direction toward (proximal) and away from (distal) a user of the device.

FIG. 1 shows a ligation device 100 for applying a ligation clip 180 to a hemorrhoid. The device 100 includes an anoscope 102 for dilating the anal cavity and a clip-applying slider unit 120 slidable into a slot 112 in the anoscope 102. The slider unit 120 may be loaded with a ligation clip 180 using an optional clip cartridge 160 and actuated to close the ligation clip 180 around the base/root of the hemorrhoid. The clips 180 may also be loaded manually. In an alternate embodiment, a ligation band may be used instead of the ligation clip 180.

The anoscope 102 has an elongated tubular body 104 with a rounded distal tip 106 and a flared proximal flange 108. A handle 110 for positioning the anoscope 102 extends proximally from the flange 108. As would be understood by those skilled in the art, the handle 110 may extend at an angle oblique to the longitudinal axis of the body 104 match the topography of the anatomy surrounding the anus. The handle 110 and/or the flange 108 may be fixed with surrounding anus area using adhesive or suture for positioning purpose. The longitudinal slot 112 of the anoscope 102 extends from a proximal end of the rounded distal tip 106 through the length of the body 104.

That is, in the present embodiment, the distal end of the anoscope 102 does not open to the interior of the anoscope 102 and the slot 112 begins proximally to the rounded tip 106. The slot 112 may extend through the flange 108 to an open proximal end of the slot 112, as shown in FIG. 1, or it may extend only partially into the flange 108, as shown in the embodiment of FIG. 23, to be explained in further detail below. The slot 112 is sized such that the slider 120 may be received therein. The anoscope 102 has C-channels 114 extending along at least a portion of the longitudinal edges of the slot 112, as shown in FIG. 4. The C-channels 114 are sized to slidingly receive rails 128 (FIG. 5) on the sides of the slider 120 so that, when the slider 120 is inserted into the slot 112, the slider 120 remains generally parallel to the longitudinal axis of the slot 112. The anoscope 102 may be made of, e.g., plastic, acrylic, glass or metal. The anoscope 102 may or may not be transparent.

Figure 5:
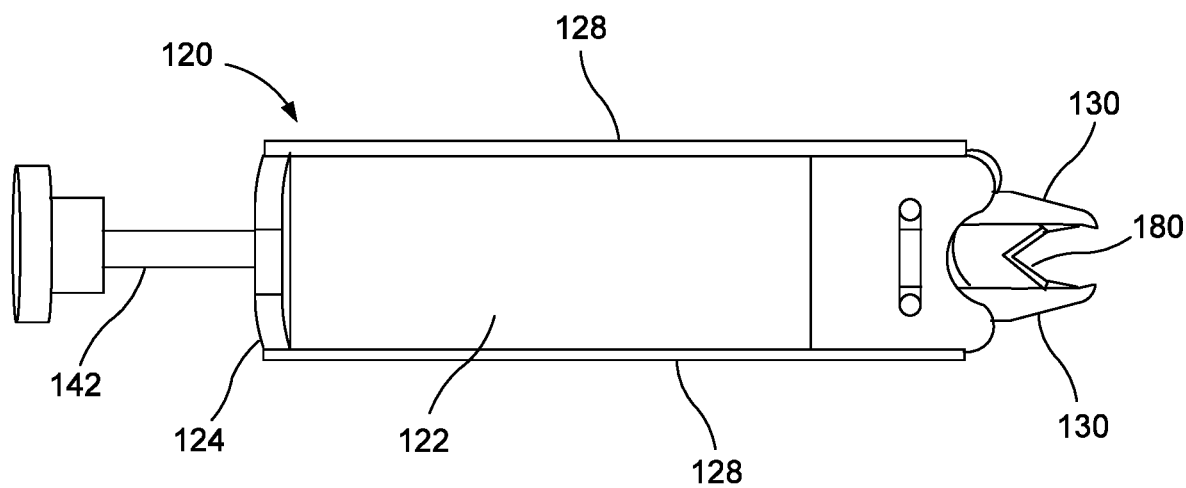
FIG. 5 shows the slider unit of FIG. 1.
Figure 6:
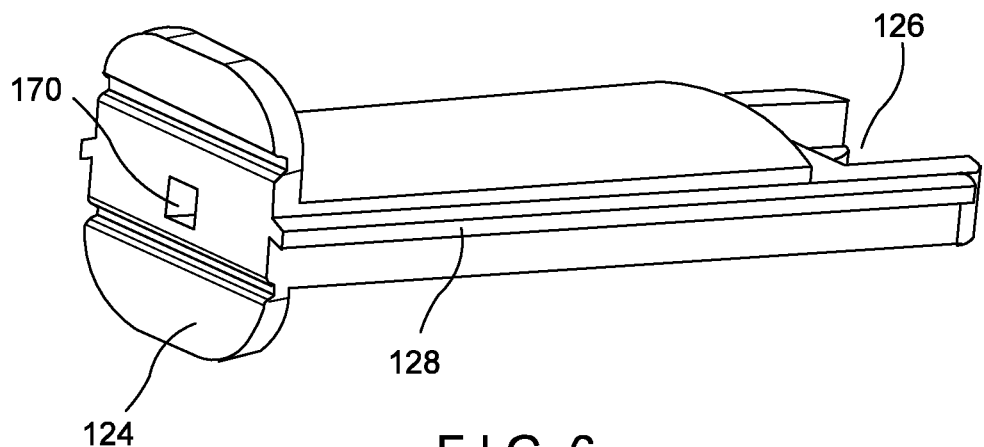
FIG. 6 shows a perspective view of the proximal end of the rectangular body of the slider unit of FIG. 5.
Figure 7:
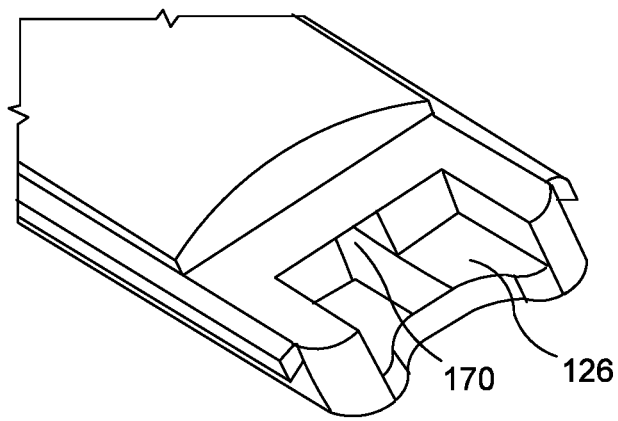
FIG. 7 shows a perspective view of the distal end of the rectangular body of the slider unit of FIG. 5.

FIG. 5 shows the slider unit 120 for closing the ligation clip 180 around the base of the hemorrhoid. The components of the slider 120 will be described herein as having a top, a bottom, two sides, a proximal end and a distal end, as labeled in FIGS. 5-6. The slider 120 includes an elongated rectangular body 122. The body 122 has a rail 128 along the length of each of the sides. The proximal end of the body 122, as shown in FIG. 6, includes a flange 124 on which the user can place two fingers to operate the device during the ligation procedure. In an alternate embodiment, a spool may be used instead of a flange. The top of the body 122 has a cavity 126 adjacent to the distal end for housing components of a clipping mechanism, as shown in FIG. 7. A working channel 170 extends from the proximal end of the body 122 through the length of the body 122 to the cavity 126, to be described in detail below.

Figure 10:
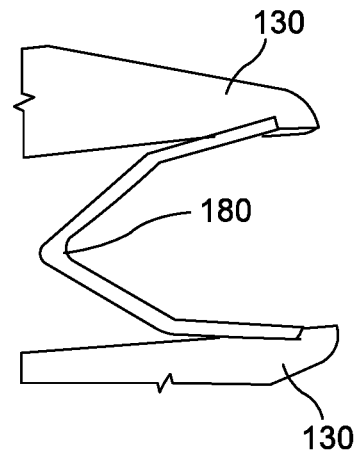
FIG. 10 shows the jaws of the slider unit of FIG. 5 with the ligation clip loaded.

The clipping mechanism includes two jaws 130 having a proximal portion disposed on opposite sides of the cavity 126 and a distal portion extending distally from the body 122. The jaws 130 are movable from an open position to a closed position. In the open position the jaws 130 are configured to hold a symmetrical substantially U- or V-shaped clip 180, as shown in FIG. 10. The ends of the V are held in notches 132 on the distal ends of the jaws 130 (see FIGS. 11-12). When the jaws 130 are moved to the closed position the ends of the V are pushed together, crimping the clip 180 closed and releasing the clip 180 from the jaws 130 when the jaws 130 are subsequently opened. The clip 180 may be made of a plastic, a metal or a material with comparable strength and deformation properties. In an alternate embodiment, ligation bands may be used instead of clips 180, the ligation bands may be made of elastomer or rubber.

Figure 9:
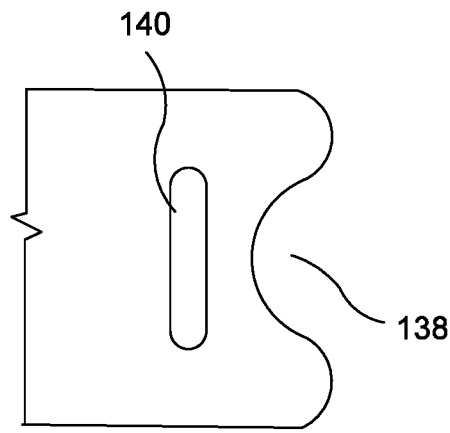
FIG. 9 shows a cap for the jaws of the slider unit of FIG. 5.
Figure 11:
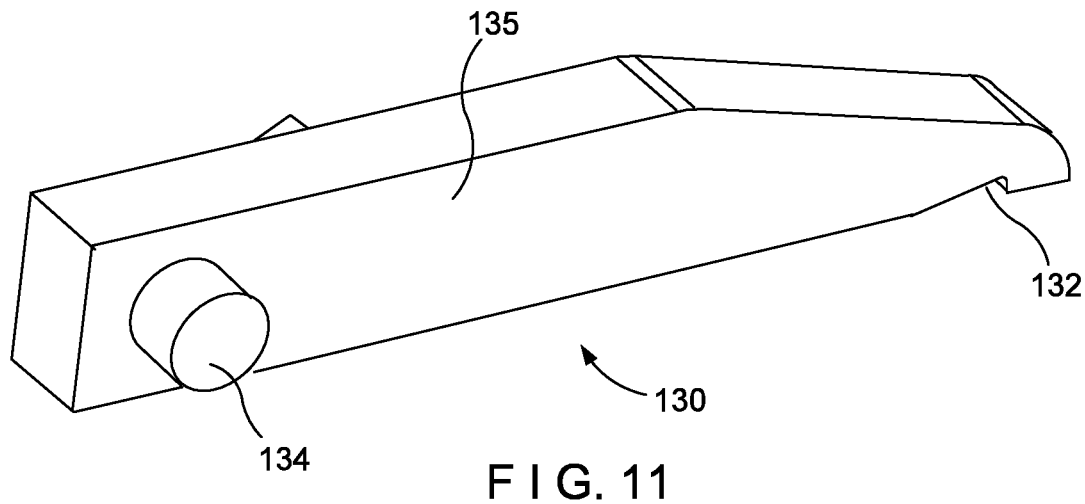
FIG. 11 shows a top view of the jaws of FIG. 5.

A cap 138 is disposed over the top of the jaws 130. The cap 138 has an interior pin slot 140 extending through its depth, as shown in FIG. 9. Each jaw 130 has a pin 134 extending from its outer surface 135 sized to slide within the slot 140 on the cap 138, as shown in FIG. 11. The pin 134 may be, e.g., cylindrical, or any other protrusion sized and shaped to be receivable in the slot 140. When the jaws 130 are in the open position the pins 134 are at opposite ends of the slot 140. Thus, it may be seen that moving the pins 134 toward one another in the slot 140 will correspondingly close the jaws 130. The cap 138 is secured to the rectangular body 122 of the slider unit 120 such that the jaws 130 are secured therebetween and the motion of the jaws 130 is limited to side-to-side movement within the slot 140.

Figure 8:
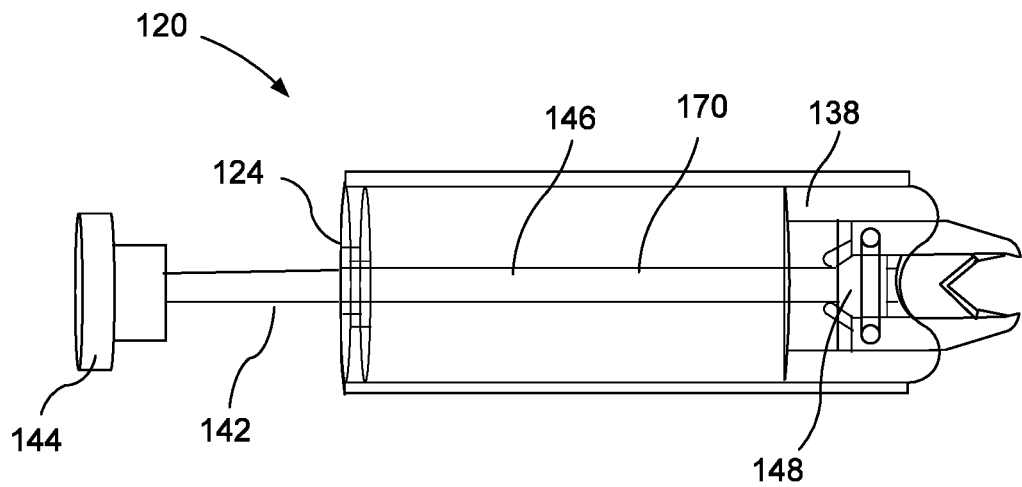
FIG. 8 shows a transparent top view of the slider unit of FIG. 5.
Figure 12:
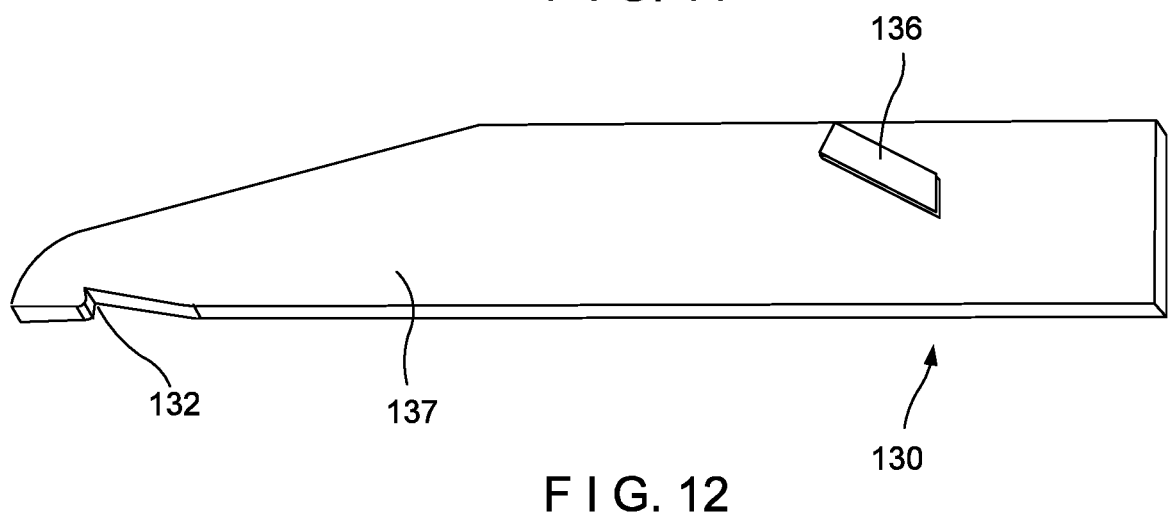
FIG. 12 shows a bottom view of the jaws of FIG. 5.
Figure 13B:
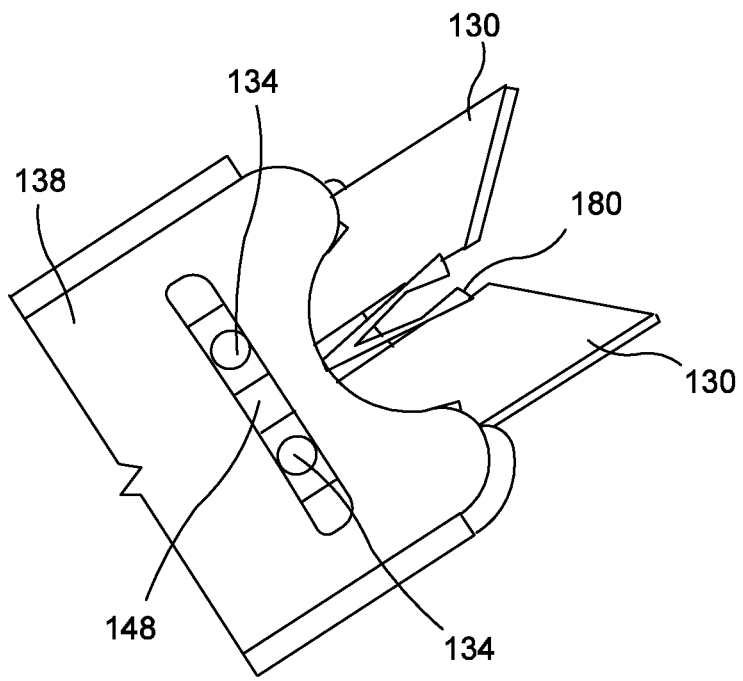
FIG. 13B shows a view of the distal end of FIG. 13A wherein the jaws are in an open position.
Figure 13C:
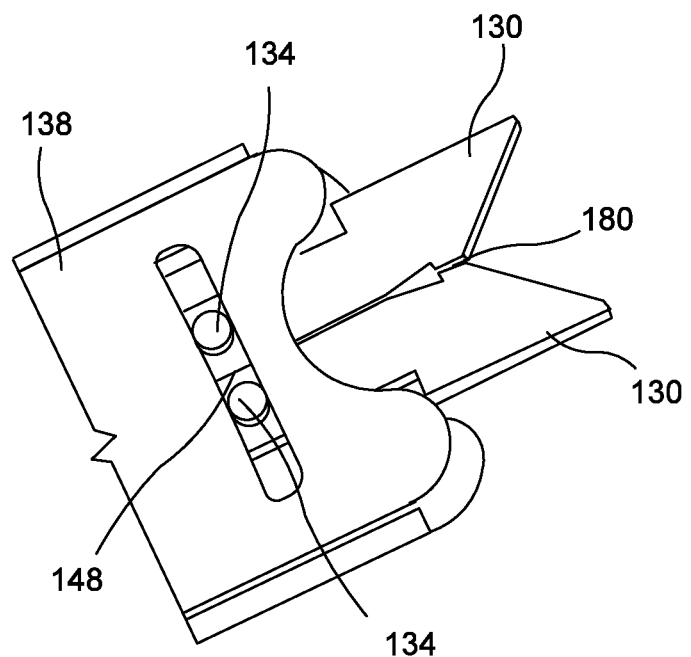
FIG. 13C shows a view of the distal end of FIG. 13A wherein the jaws are in a closed position.
Figure 15:
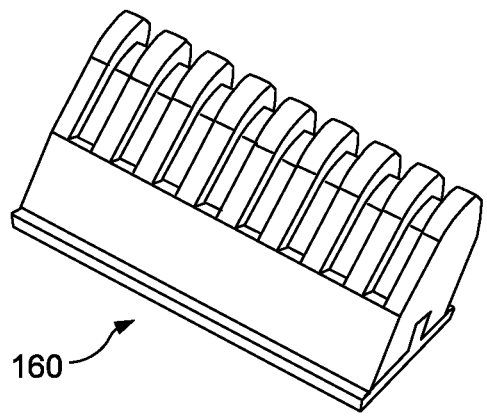
FIGS. 15-19 show views of the components of the clip cartridge of FIG. 2.
Figure 16:
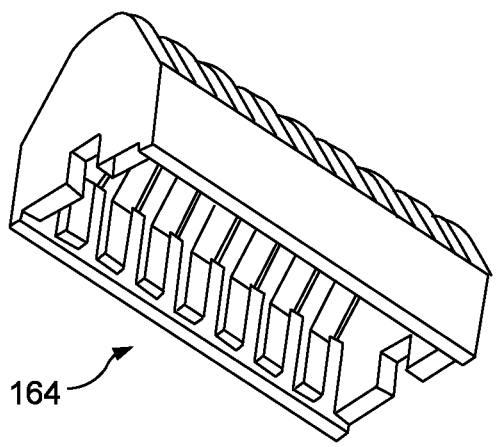
Figure 17:
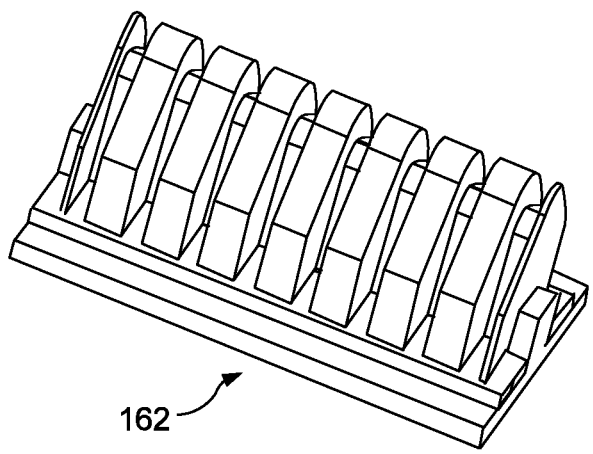

An inner surface 137 of each of the jaws 130 has a rib 136 extending therefrom, as shown in FIG. 12. The rib 136 is angled obliquely to the jaw and is configured to couple to a distal head 148 of a plunger 142 (see FIG. 13A), as will be explained in further detail below. The plunger 142 has a proximal flange 144 and an elongated shaft 146 extending from the flange 144 to the distal head 148. The shaft 146 is sized and shaped to slide within the working channel 170 of the rectangular body 122, as shown in FIG. 8. The proximal flange 144 is sized and shaped to support the thumb of an operating physician during the ligation procedure.

Thus, it may be seen that an operating physician may operate the slider unit 120 using a thumb on the proximal flange 144 of the plunger 142 and two fingers on the proximal flange 124 of the rectangular body 122. In an alternate embodiment, the plunger 142 has a thumb ring instead of a flange. Pushing the plunger 142 distally with respect to the body 122 correspondingly moves the distal head 148 of the plunger 142 distally. The distal head 148 extends from the shaft 146 and has a triangular shape with two flared sides and a distal side, as shown in FIG. 14. Each of the flared sides has a top channel 150 extending along its length. The channel 150 is sized to receive the rib 136 extending from the bottom of the jaw 130. The channel 150 and the rib 136 are described as having an essentially linear profile, however, any shape or profile may be used to slidingly lock the two components.

The jaws 130 are operable to move between the open position and the closed position by the motion of the plunger 142. As noted previously, the jaws 130 have pins 134 disposed in the slot 140 of the cap 138. The slot 140 extends laterally with respect to the longitudinal axis of the device, i.e., side-to-side. Thus, the jaws 130 are locked in the proximal/distal direction and movable only laterally. The ribs 136 of the jaws 130 are slid within the channels 150 of the distal head 148 at the same oblique angle. For example, the ribs 136 and channels 150 may be at an angle of approximately 45° to the longitudinal axis of the slider 112. When the jaws 130 are open the plunger 142 is at its most proximal position and the ribs 136 are situated at the distal end of the channels 150 of the distal head 148.

As the plunger 142 moves distally the ribs 136 remain fixed in the proximal/distal direction (because of the pins 134 in the slot 140) yet get pushed laterally as the channel 150 slides over the ribs 136. In other words, the rib 136 provides lateral movement which will result in the open position and the closed position of the jaws 130, while the pin 134 maintains parallel and simultaneous movement between the jaws 130. When the plunger 142 is advanced to its most distal position the pins 134 are brought into close contact and the jaws 130 are substantially closed. The above described mechanism provides for generally parallel closing of the jaws 130 to help apply a substantially uniform pressure to the base of a hemorrhoid. Further, until the jaws 130 are completely closed, the plunger 142 may be moved proximally to reopen the clip 180 and reposition the device 100 if necessary.

When a clip 180 is loaded between the jaws 130 it will deform into a substantially flat (closed) shape as the jaws 130 are closed. During a ligation procedure the clip 180 is closed around the base of a hemorrhoid to constrict the blood flow thereto. A camera 152 on the distal end of the distal head 148 of the plunger 142 may be used to visualize the ligation procedure, as shown in FIGS. 13A-13C and 14. The field of vision of the camera 152 extends out the distal end of the slider 120.

Figure 18:
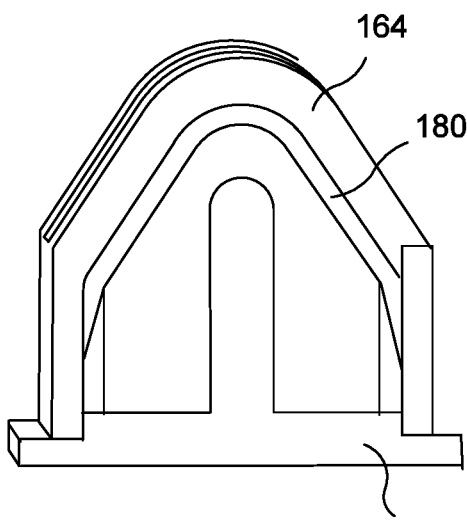
Figure 19:
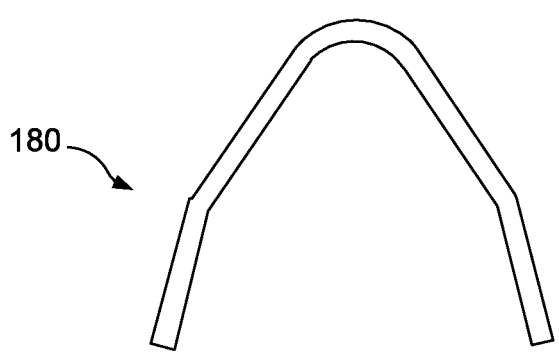
Figure 21B:
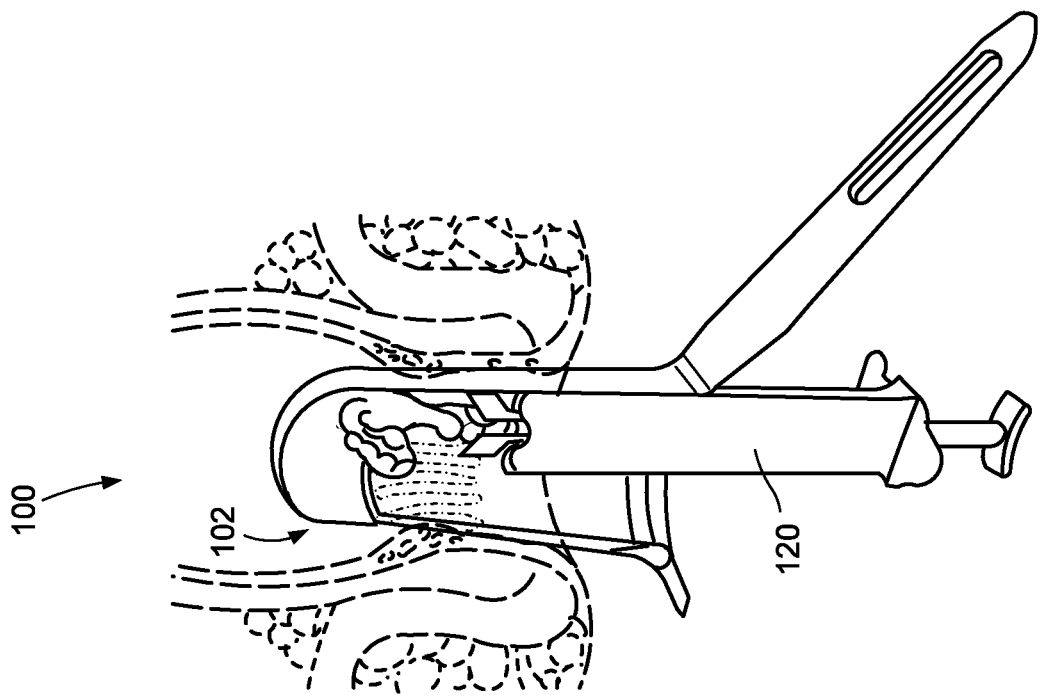
FIG. 21B shows a view of the slider unit of the ligation device of FIG. 1 inserted into the anoscope.
Figure 21A:
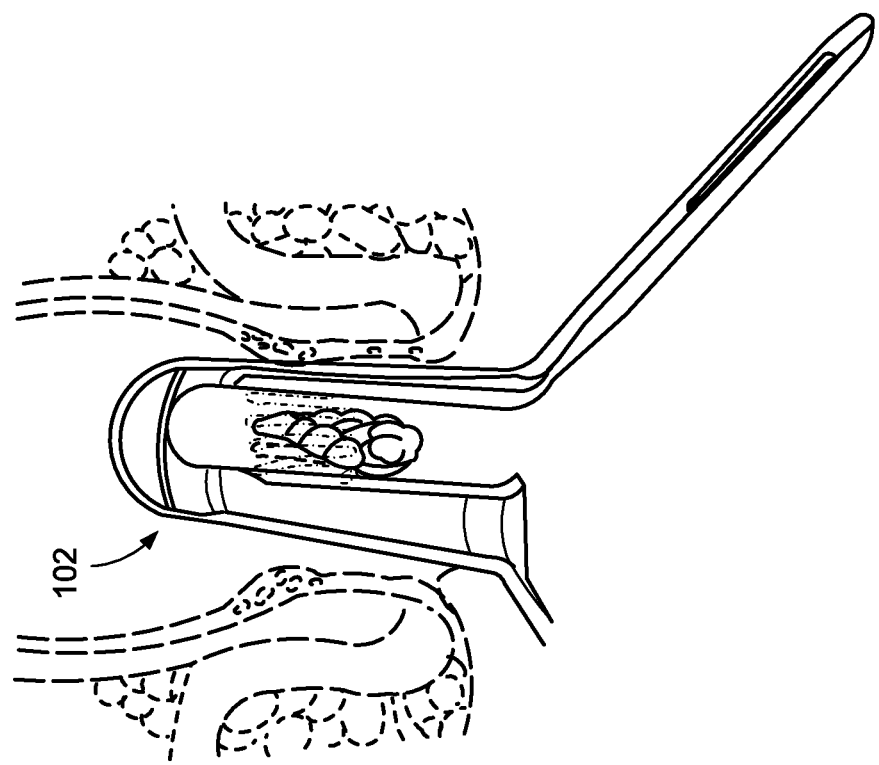
FIG. 21A shows a view of the anoscope of the ligation device of FIG. 1 inserted into the anus.
Figure 21D:
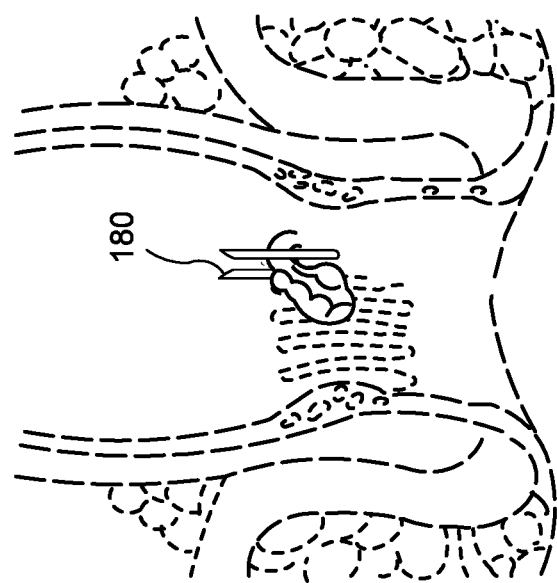
FIG. 21D shows a view of the ligation clip of the ligation device of FIG. 1 deployed at root of the hemorrhoid.
Figure 21C:
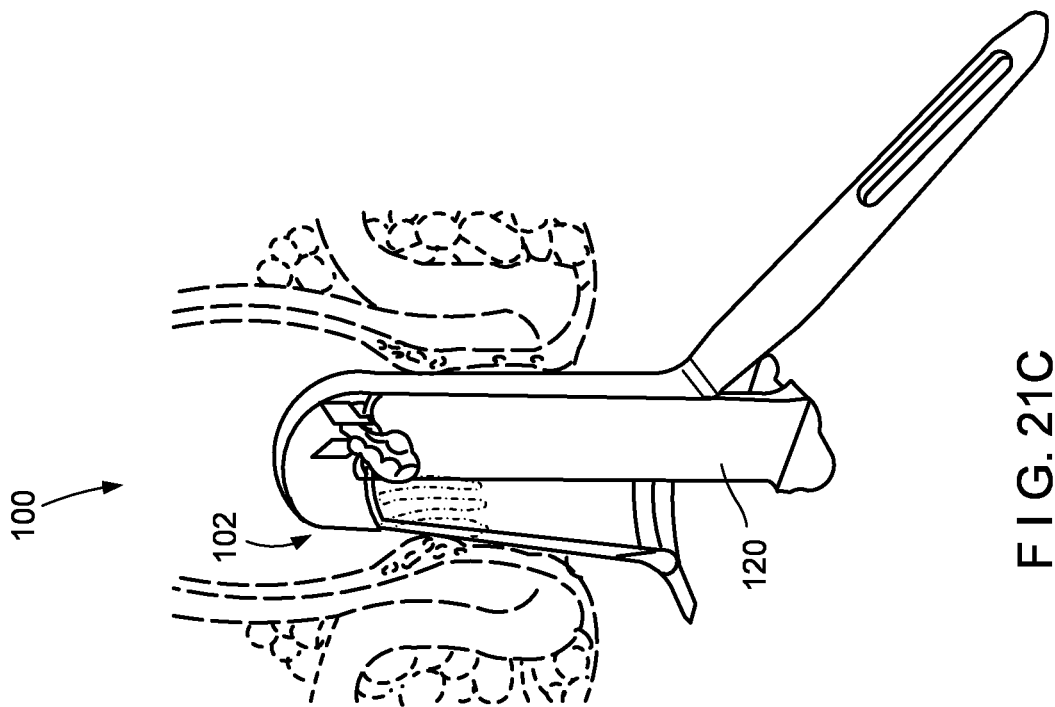
FIG. 21C shows a view of the ligation clip of the ligation device of FIG. 1 closed around the hemorrhoid.

A clip 180 may be loaded in the slider 120 using the clip cartridge 160, as shown in FIGS. 15-19. The clip cartridge 160 has a lower housing 162 and upper housing 164. The lower housing 162 has a plurality of slots extending laterally along its length for holding a plurality of ligation clips 180. The upper housing 164 is pushed over the lower housing 162 to force the clips 180 slightly closed by applying stress on the ends of the V-shape, as shown in FIG. 18. The portion of the upper housing 164 above the clips 180 has channels cut thereinto to expose the middle of the inverted V-shape. The slider 120 may be inserted into one of the channels of the upper housing 164 with the jaws 130 in the open position to position the jaws 130 around the V. The ends of the V-shape are locked into the notches 132 on the jaws 130, allowing for removal from the cartridge 160.

FIG. 22 shows a device 300 comprising an anoscope 302 according to a second exemplary embodiment for use with the slider unit 120 (not shown). The anoscope 302 is similar to the anoscope 102, however, the anoscope 302 has three slots 312 for receiving hemorrhoids therein. In this way, during a ligation procedure the operating physician need not reorient the anoscope 302 in the anal cavity of the patient to treat multiple hemorrhoids. The physician may simply reload a clip 180 in the slider 120 after treating a first hemorrhoid in a first slot 312 and treat remaining hemorrhoids in the second and/or third slot 312.

Figure 24A:
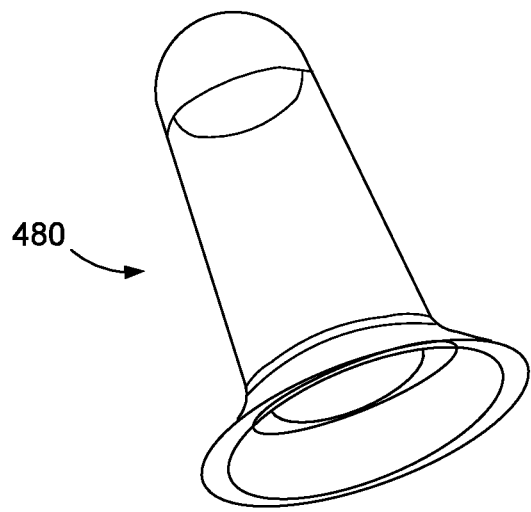
FIG. 24A shows a dilator for use with an anoscope.
Figure 24B:
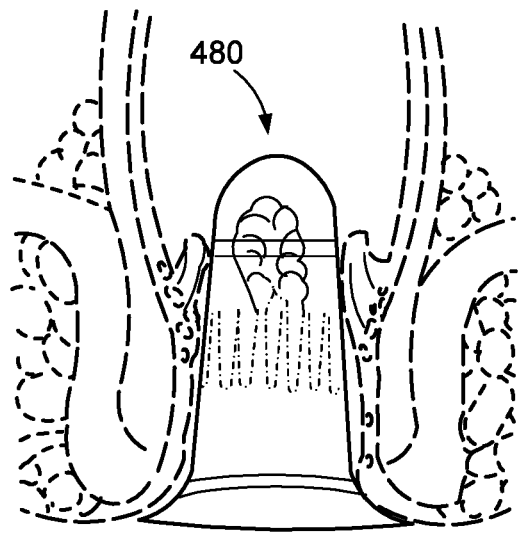
FIG. 24B shows a dilator for use with an anoscope inserted into an anus.

FIG. 23 shows a device 400 comprising an anoscope 402 according to a third exemplary embodiment for use with the slider unit 120 (not shown). The anoscope 402 is similar to the anoscope 102, however, the slot 412 of the anoscope 402 extends distally into a rounded distal tip 406 instead of being limited to the elongated tubular body 404. In this way, the operating physician may capture a hemorrhoid with the anoscope 402 at a location more distal than can be accessed using the anoscope 102. However, use of the anoscope 402 during a ligation procedure typically requires a dilator 480 prior to insertion of the anoscope 402 in the anal cavity, as shown in FIGS. 24A-24B.

Figure 25:
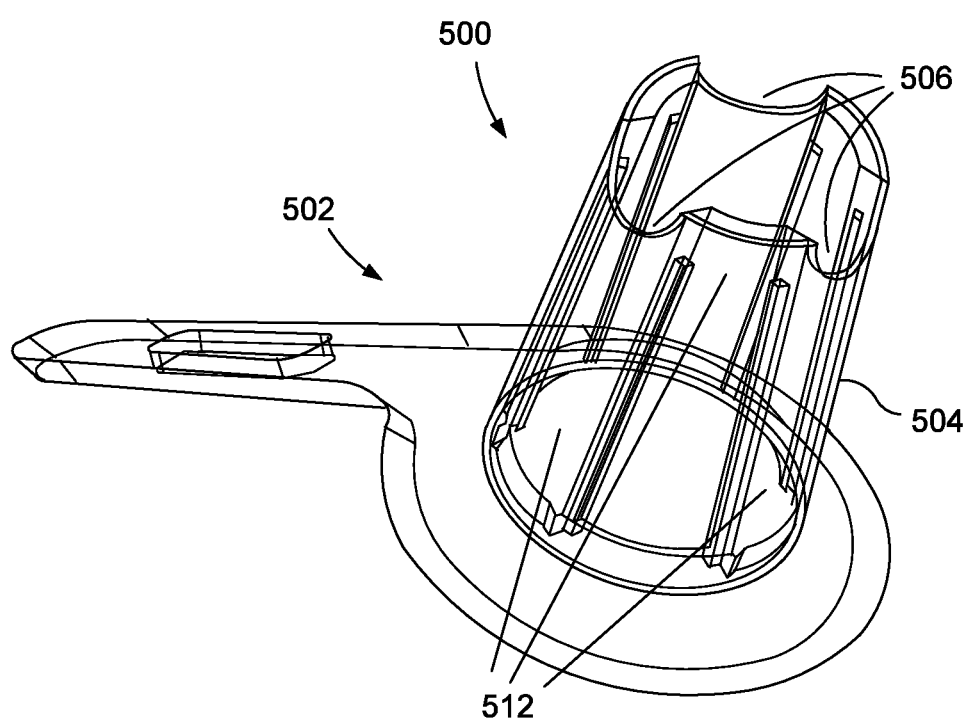
FIG. 25 shows a device comprising an anoscope according to a fourth exemplary embodiment.
Figure 26B:
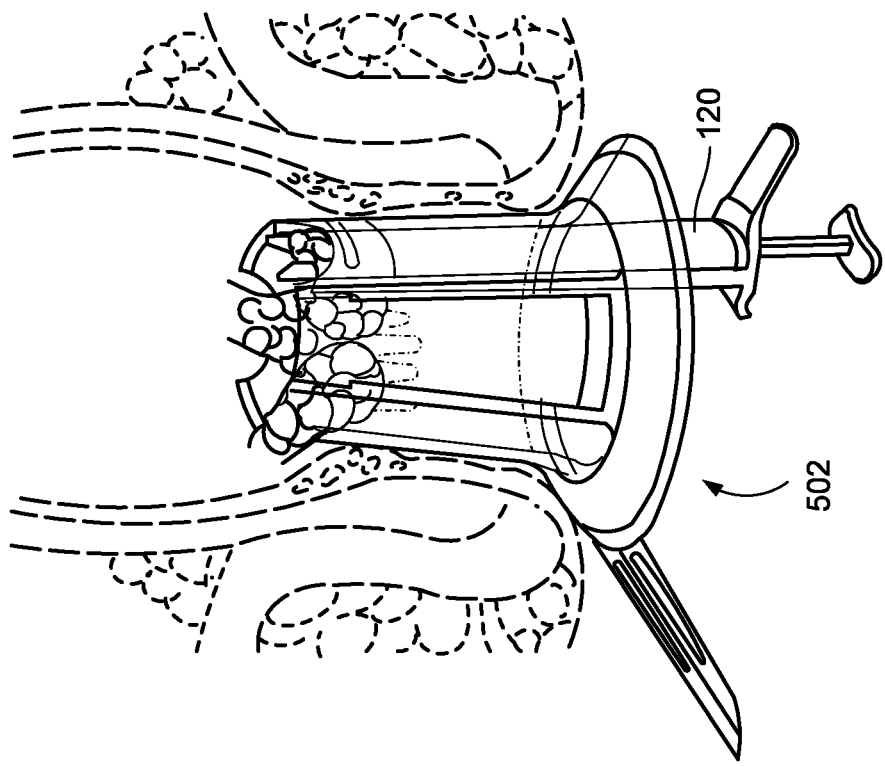
FIG. 26B shows a view of the slider unit of the ligation device of FIG. 1 inserted into the anoscope of FIG. 25.
Figure 26A:
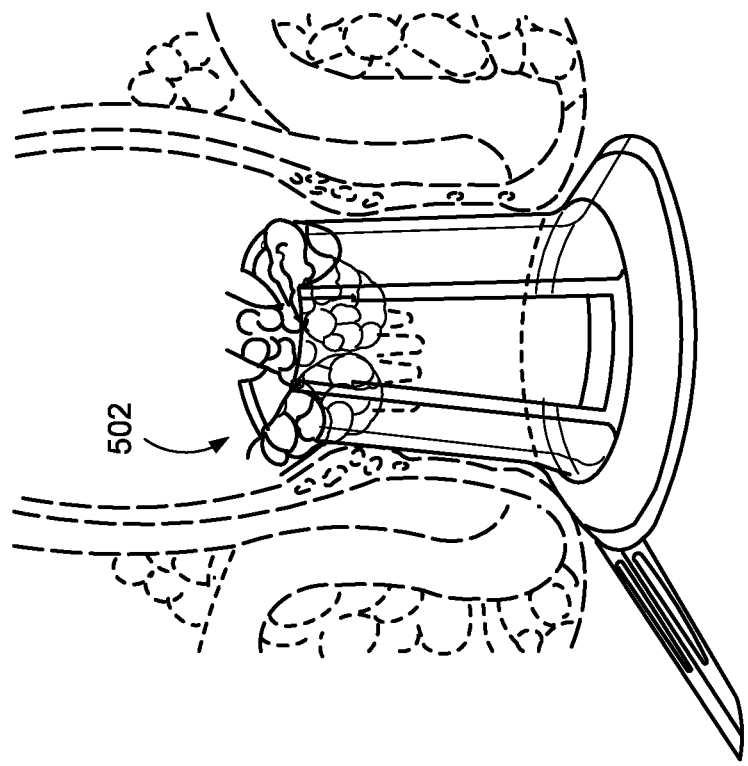
FIG. 26A shows a view of the anoscope of FIG. 25 inserted into the anus.
Figure 26D:
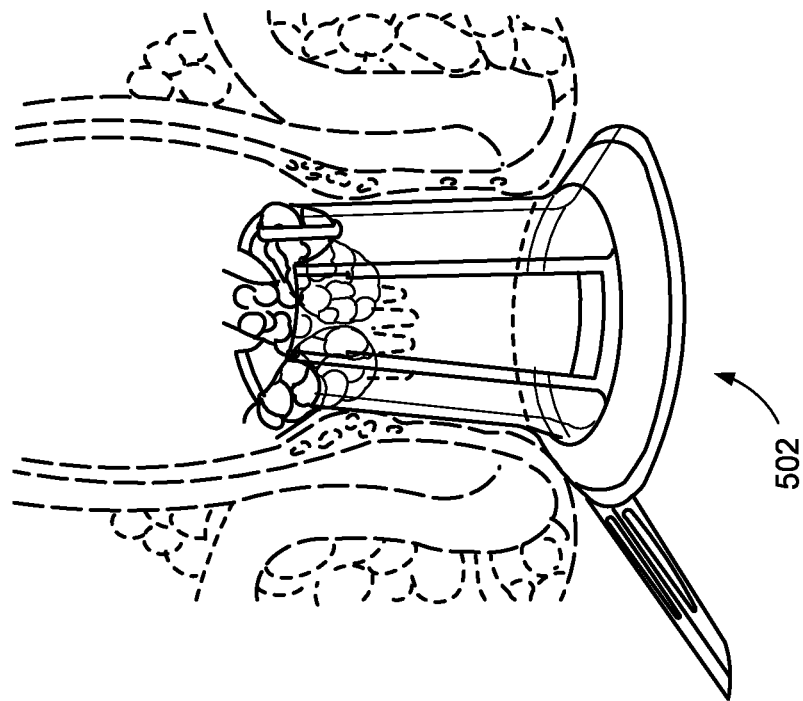
FIG. 26D shows a view of the ligation clip of the ligation device of FIG. 1 deployed at root of the hemorrhoid.
Figure 26C:
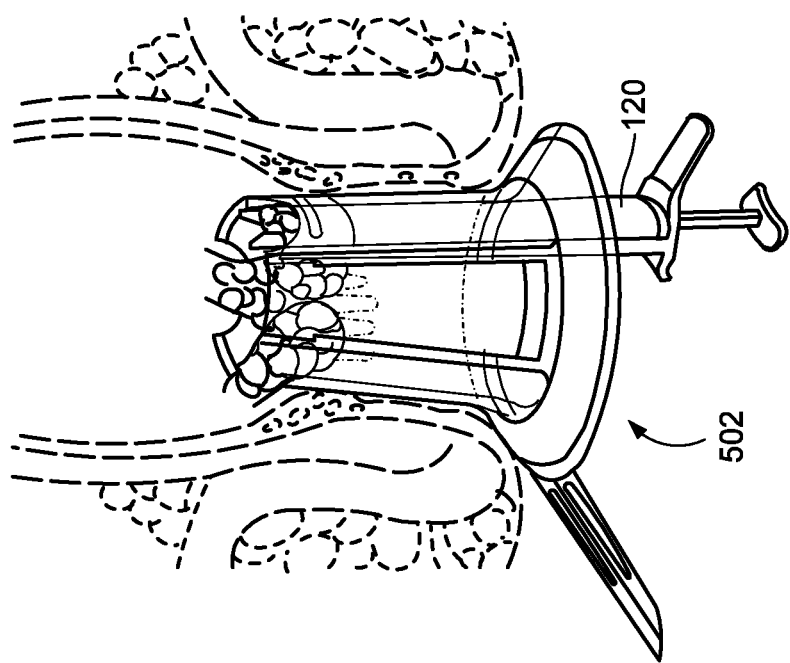
FIG. 26C shows a view of the ligation clip of the ligation device of FIG. 1 closed around the hemorrhoid.
Figure 26E:
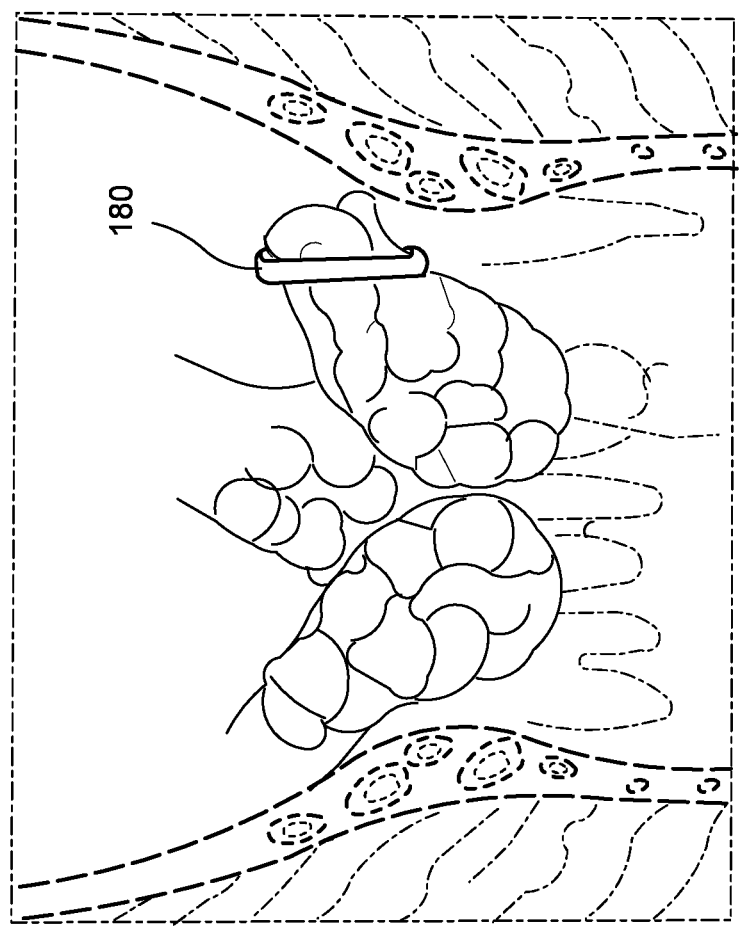
FIG. 26E shows a view of the ligation clip of the ligation device of FIG. 1 on the hemorrhoid after the removal of the anoscope of FIG. 25.

FIG. 25 shows a device 500 comprising an anoscope 502 according to a fourth exemplary embodiment for use with the slider unit 120 (not shown). The anoscope 502 has a similar basic shape as the prior embodiments. However, the anoscope 502 does not have a distal tip. Instead, the anoscope 502 has an elongated tubular body 504 with an open distal end. The body 504 has three U-channels 506 in the open distal end of the tubular body 504 for receiving hemorrhoids therein during a ligation procedure. After expanding the anal cavity with a dilator, e.g., the dilator 480, the anoscope 502 may be inserted so that the hemorrhoid(s) enter into one or more of the U-channels 506, as shown in FIG. 26A-26E.

Figure 37:
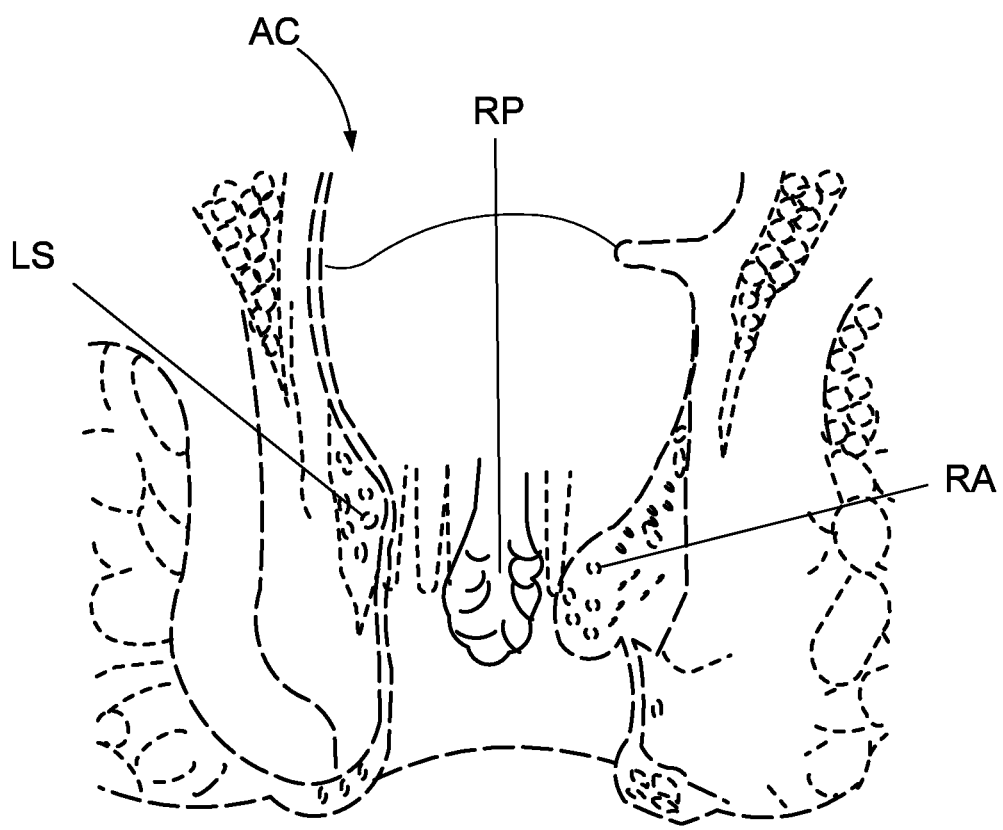
FIG. 37 shows an anal canal with 3 main cushions of hemorrhoidal tissue.

The anoscope 502 has three slot portions 512 similar to the anoscope 302, however the slot portions 512 are formed in the portions of the body 504 proximal to the U-channels 506. In other words, the body 504 is solid about its circumference without having fully open slots, as seen in the previously described embodiments. Thus, the slots 512 are aligned with the U-channels 506 so that insertion of the slider unit 120 therein will bring the jaws 130 to the base of the hemorrhoid. FIG. 37 shows an anal canal (AC) with internal hemorrhoids, the internal hemorrhoids have 3 main cushions which are situated in left lateral (LS), right posterior (RP, most common) and right anterior (RA) areas of the anal canal. The anoscope 502 has three slots defined such that the hemorrhoids from these areas always fall into these slots.

FIG. 27 shows a device 600 comprising an anoscope 602 according to a fifth exemplary embodiment, the anoscope 602 can be used with an applicator 620 of FIG. 28 (not shown). The anoscope 602 is similar to the anoscope 502, in that it has an open distal end with three U-channels 606 formed in the body 604. Thus, the dilator 480 may be used to expand the anal cavity. However, in lieu of slots, the body 604 has three working channels 612 for use with the clip applicator 620, as shown in FIG. 28, to be described in detail below. The working channels 612 extend through the length of the body 604 to the middle of the U-shape of the channels 606.

Figure 31:
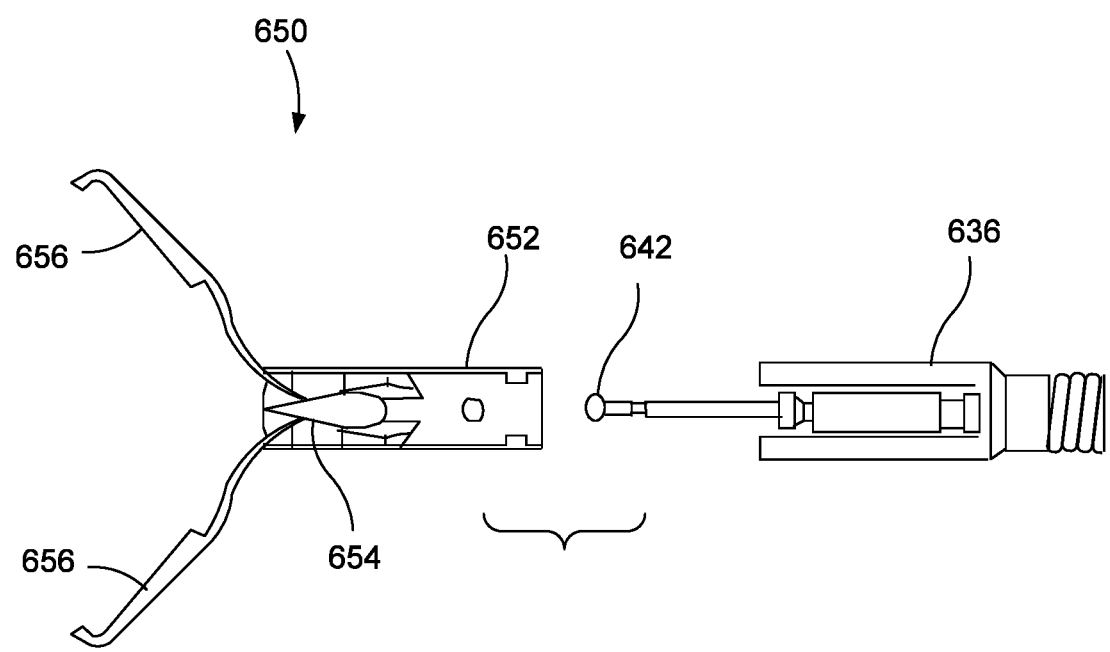
FIG. 31 shows a distal end of the clip applicator of FIG. 28 and a clip assembly prior to engagement.
Figure 32C:
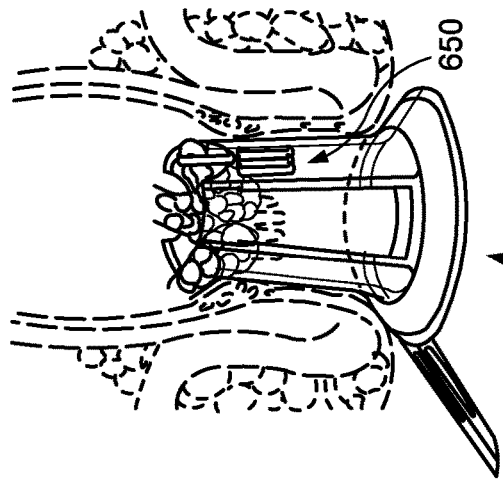
FIG. 32C shows a view of a clip assembly of the applicator of FIG. 28 deployed on the hemorrhoid after removal of the clip applicator of FIG. 28.
Figure 32D:
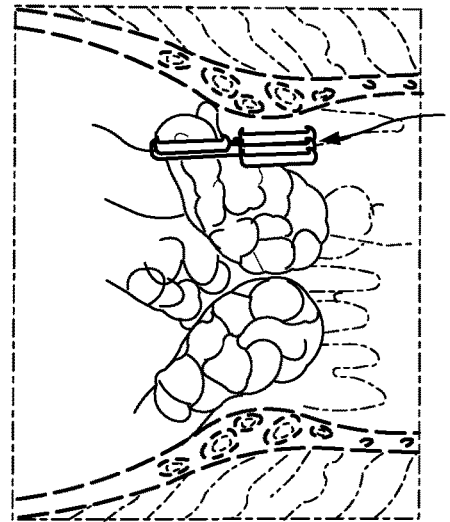
FIG. 32D shows a view of the clip assembly of the applicator of FIG. 28 on the hemorrhoid after the removal of the anoscope of FIG. 27.
Figure 32B:
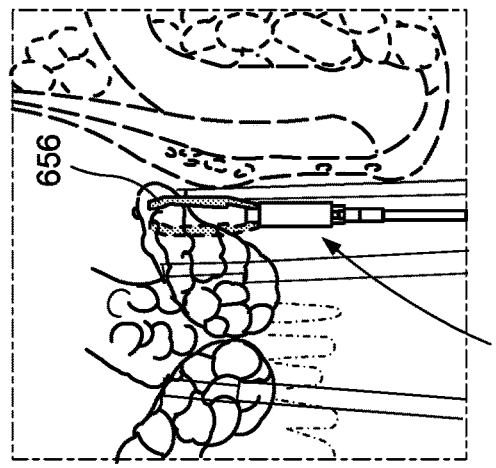
FIG. 32B shows a view of jaws of the clip applicator of FIG. 28 closing about the base of the hemorrhoid.
Figure 32A:
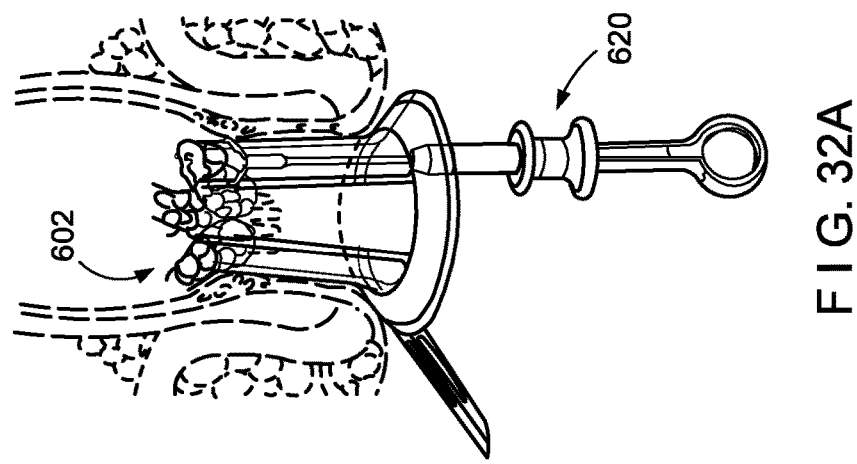
FIG. 32A shows a view of the clip applicator of FIG. 28 inserted through the anoscope of FIG. 27 inserted into the anus.

The clip applicator 620 includes a handle portion 622 with a thumb ring 624 on a proximal end. The handle 622 has a longitudinal slot 626 running down a portion of the length of the handle 622 distal to the thumb ring and extending to a tubular distal portion 628 of the handle 622. A spool 630 is disposed around the handle 622 and is slidable between the proximal end and the distal end of the slot 626. The spool 630 may be spring-biased with respect to the handle 622 when it is slid to the distal end, i.e., a spring-contracting position. A thin flexible coil 634 is attached (i.e., crimped or welded) to a coil retainer 644 and extends distally therefrom. A coil cap 632 is attached to the distal end of the distal portion 628 of the handle 622. The coil cap 632 ensures that the coil retainer 644 remains inside the coil cap 632, thus ensuring that the coil 634 and retainer 644 are connected to the handle 622. The flexible coil 634 terminates at an open distal end 636 that is coupled to a clip assembly 650, as shown in FIG. 31, to be explained in detail below.

A core wire 638 extends through the interior of the clip applicator 620, passing through the interiors of the spool 630, the distal portion 628 of the handle 622, the coil retainer 632 and the coil 634, and is slidable therewithin. The core wire 638 of this embodiment is attached to the spool 630 via a crimp sleeve 640 held in a cylindrical slot in the proximal end of the spool 630. When the spool 630 is in a proximal position the core wire 638 extends to the distal end 636 of the coil 632. When the spool 630 is pushed to a distal position the core wire 638 extends a distance past the distal end 636 of the coil 632. The core wire 638 has a clip assembly attachment 642 at its distal end that engages the clip assembly 650. The clip assembly attachment 642 has a larger cross-section than the core wire 636 and may be, e.g., a spherical nub.

The clip assembly 650 includes a capsule 652 housing a yoke 654 slidable therewithin. The yoke 654 is attached to two clip jaws 656 extending through two holes at the distal end of the capsule 652. Each of the jaws 656 has a curved proximal portion that extends out of the hole when the yoke 654 is in a distal position and is pulled within the capsule 652 when the yoke is drawn to a proximal position via the core wire 638. Each of the jaws 656 has a distal portion which, in combination, are used to grasp the hemorrhoid. The proximal portion of each of the jaws 656 has a curved shape such that, when the proximal portion is pulled within the capsule 652, the distal portions of the jaws 656 close toward one another. When the yoke 654 is in the proximal position the jaws 656 are substantially closed.

Figure 30:
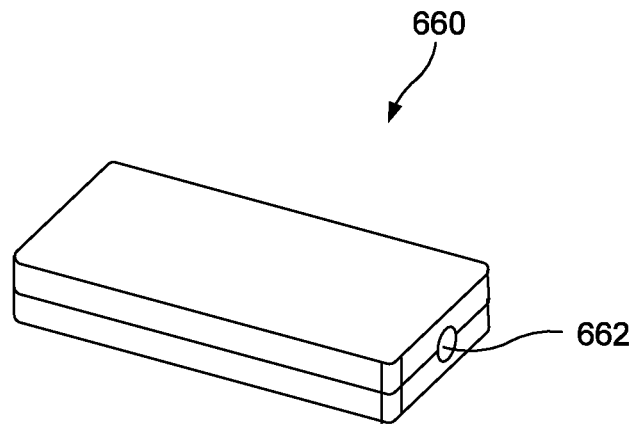
FIG. 30 shows a clip cartridge for use with the clip applicator of FIG. 28.

FIG. 30 shows a clip cartridge 660 for housing the clip assembly 650 prior to loading the clip assembly 650 on the clip applicator 620. The clip cartridge 660 of this embodiment is generally rectangular with an access hole 662 on one side. To engage the clip applicator 620 with the clip assembly 650 the distal end 636 of the coil 632 is inserted into the access hole 662. The spool 630 is pushed to the distal position, thus pushing the core wire 638 and clip assembly attachment 642 distally to engage the yoke 654. As may be seen in FIG. 31, the yoke 654 is shaped with an opening that is slightly smaller than the cross-section of the clip assembly attachment 642. The yoke 654 is sufficiently flexible to allow the clip assembly attachment 642 to pass through the opening when a sufficient force is applied. A corresponding disengagement of the clip assembly attachment 642 with the yoke 654 may be accomplished by pulling the spool 630 proximally with a substantially similar force.

Once the yoke 654 and the clip assembly attachment 642 have engaged, the spool may be moved proximally to close the jaws 656 (but not so far proximally as to disengage the core wire 638) and withdraw the clip assembly 650 from the clip cartridge 660. Once loaded, the clip applicator 620 may be used with the anoscope 602 to treat one or more hemorrhoids.

FIGS. 32A-32D show views of the ligation procedure using the anoscope 602 and the clip applicator 620. The anoscope 602 is inserted into the anal cavity in a manner substantially similar to that described with respect to the anoscope 502. It may be seen that the clip assembly 650 and the coil 632 are sized to be received in the working channels 612 of the anoscope 602. The jaws 656 are held closed during the insertion of the clip assembly 650. When the clip applicator 620 has been inserted sufficiently distally into one of the working channels 612 such that the jaws begin protruding into the U-channel 606 the jaws 656 are opened and positioned about the hemorrhoid by pushing the spool 630 distally with respect to the handle 622. The jaws 656 may then be closed about the base of the hemorrhoid by pulling the spool 630 proximally.

The proximal pulling of the spool 630 brings the yoke 654 to a proximal position in the capsule 652 of the clip assembly 650. Further proximal pulling of the spool 630 disengages the clip assembly attachment 642 from the yoke 654. The clip applicator 620 may optionally include a clicking or other feedback mechanism to notify the physician when disengagement is imminent. Once the clip has been applied, the clip applicator 620 is withdrawn from the working channel 612, leaving the clip assembly 650 attached over and constricting the base of the hemorrhoid. If more hemorrhoids remain to be treated in one or more of the other U-channels 606 of the anoscope 602 the clip applicator 620 may be reloaded with a second clip assembly 650 and the procedure may be repeated.

Figure 33A:
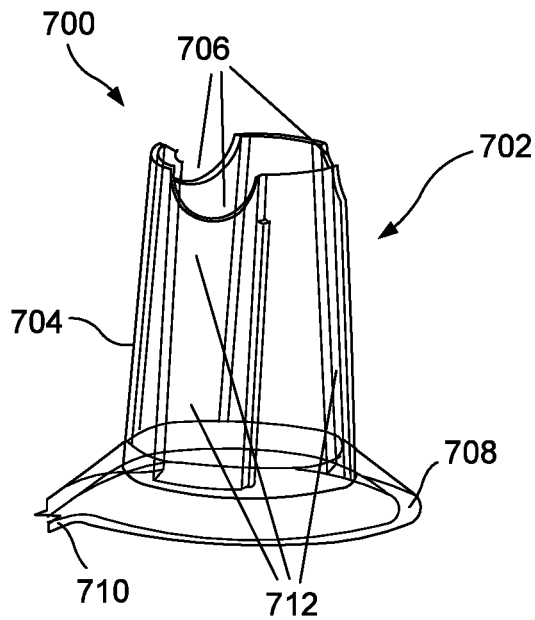
FIG. 33A shows a device comprising an anoscope having a radially adjustable tubular body.
Figure 33B:
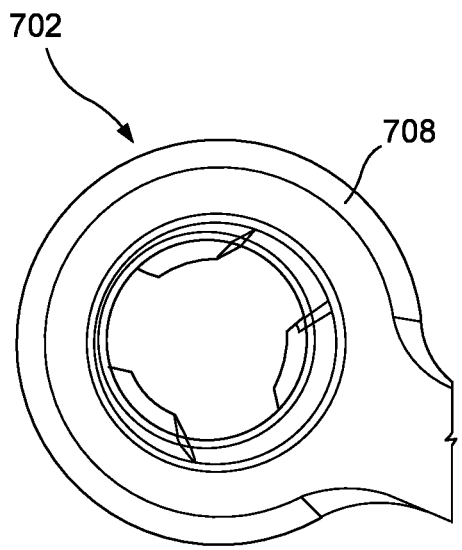
FIG. 33B shows a proximal view of a rotation of the anoscope of FIG. 33A.

FIGS. 33A-33B show a device 700, comprising an anoscope 702 having a radially adjustable tubular body, the anoscope 702 can be used with the slider unit 120 of FIG. 1 (not shown). The basic anoscope shape of the anoscope 702 corresponds to that of the anoscope 502, wherein the anoscope 702 has an elongated tubular body 704 with an open distal end, the body 704 having 3 channels 706 and 3 slots 712 for the insertion of slider unit 120. Additionally, the anoscope 702 has a flange 708 and a handle 710. The body 704 may be rotated independently from the flange 708 and the handle 710 of the anoscope 702 using a circumferentially slidable coupling between the body and the flange. However, any anoscope shape having a complete flange may implement a radially adjustable tubular body. In other words, if the slot for the slider unit does not extend through the flange then the anoscope may be radially adjustable—if the slot extends through the flange, rotating the body would offset the body slot from the flange slot. Thus, the anoscopes 402, 502 and 602 may have the radially adjustable body feature.

Figure 34:
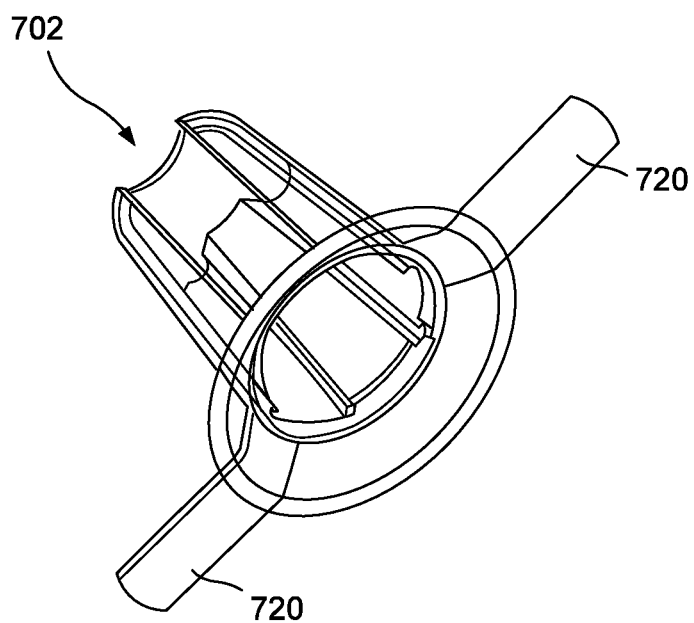
FIG. 34 shows an anoscope with sticking tape.

FIG. 34 shows the anoscope 702 having sticking tape 720 to paste the anoscope 702 to the body of the patient. The sticking tape 720 may be used with any of the anoscopes described previously. However, when using the tape with anoscopes that do not have the radially adjustable feature (e.g., the anoscope 102 and the anoscope 302), the physician will be unable to adjust the positioning of the anoscope and anoscope slots/channels without removing the sticking tape 720 first.

FIG. 20 shows a method 200 for performing a ligation procedure using the device 100, the device 300, the device 400, the device 500, the device 600, and the device 700. The method 200 will be described in conjunction with FIGS. 21A-21D, FIGS. 26A-26E, and FIGS. 32A-32D. The following description below of the method 200 refers to the device 100, however, as one pf ordinary skills in the art will ascertain, the method 200 is applicable to the above-mentioned exemplary embodiments of the devices.

In step 205, the patient is positioned in a prone jack knife position or lithotomy position.

In optional step 210, a dilating procedure may be performed to dilate the anal cavity of the patient. For the dilating procedure a separate dilator is inserted into the anal cavity and rectum of the patient. The dilator may be left in the anal cavity for a predetermined amount of time, or until the physician decides that the anal cavity has been properly dilated. After proper dilation, the dilator may be removed from the anal cavity.

In step 215, the anoscope 102 is inserted into the anal cavity and rectum of the patient. The distal tip 106 may first push the hemorrhoidal tissue distally, such that, when the slot 112 is brought into a position to receive the hemorrhoidal tissue therein, the base of the hemorrhoid is exposed on a proximal side. The anoscope 102 is advanced until the flared proximal flange 108 abuts the perineum and rotated to allow the target hemorrhoid to fall into the slot 112.

In optional step 220, the handle 110 and/or the flanges 108 of the anoscope 102 may be pasted or sutured to the anal cavity or rectum of the patient for positioning purposes. In one exemplary embodiment, the anoscope (e.g., the anoscope 502, the anoscope 602, and the anoscope 702) may be inserted into the anal cavity with the dilator inserted therethrough.

In step 225, the clip 180 is loaded in the jaws 130 of the slider 120. The clip 180 may be loaded using the clip cartridge 160 or may be loaded manually. In step 230, the slider 120 is inserted into the slot 112 by sliding the rails 128 in the channels 114. The slider 120 is advanced distally until the jaws 130 (with the clip 180 therein) substantially surround the hemorrhoid.

In step 235, the plunger 142 is pushed distally, forcing the jaws 130 closed around the hemorrhoid and deforming the clip 180 into a flat, constricted state around the base of the hemorrhoid. In step 240, the plunger 142 is pulled proximally back to its original position, opening the jaws 130 and releasing the deformed clip 180 on the hemorrhoid.

In step 245, the physician makes a determination on whether more hemorrhoids need to be treated. If the physician determines that more hemorrhoids need to be treated, the physician will move onto step 250. If the physician determines that no more hemorrhoids need to be treated, in step 255 the physician may remove the device 100 from the anal cavity and end the procedure.

In step 250, if the device used in the procedure contains a single slot (e.g., the device 100 and the device 400), the method moves onto step 260. If the device used in the procedure contains multiple slots (e.g., the device 300, the device 500, the device 600, and the device 700), the method moves onto step 265.

In step 260, the physician may withdraw the slider portion 120 only, leaving the anoscope 102 inserted in the anal cavity, and reorient the anoscope 102 to receive a further hemorrhoid in the slot 112. Subsequently, the steps 215-245 are repeated until no further hemorrhoids remain to be treated. In an alternate embodiment, the anoscope 102 may be removed and repositioned to receive the further hemorrhoid in the slot 112. Subsequently, the steps 215-245 are repeated until no further hemorrhoids remain to be treated.

In step 265, the slider 120 may be withdrawn and placed into a second slot (e.g., a second slot 312, a second slot 412, and a second slot 512) to constrict a second ligation clip 180 around the base of the further hemorrhoid. Subsequently, the steps 225-245 are repeated until no further hemorrhoids remain to be treated. In an alternate embodiment, in step 265, the applicator 620 may be withdrawn and placed into a second working channel 612 to constrict a second clip assembly 650 around the base of the further hemorrhoid. Subsequently, the steps 225-245 are repeated until no further hemorrhoids remain to be treated. Once the procedure is complete, the physician withdraws the device 100 in step 255.

Other hemorrhoid treatment methods may be used in conjunction with the aforementioned embodiments of the anoscope and clip-applying means. For example, FIG. 35 shows an electrocautery loop 810 being extended from a hollow catheter 820. Electrocautery loops 810 may be energized when the loop is constricted about the hemorrhoid. Thus, the electrocautery loop 810 may cut the hemorrhoid and also cauterize the remaining tissue, reducing or eliminating bleeding. In another example, FIG. 36 show an adjustable band 910 for ligation. The adjustable band 910 wraps around the hemorrhoid. An extended portion 920 of the adjustable band 910 is pulled in a direction of arrow T to tighten the hemorrhoid at a node. The extended portion 920 may be cut off once the adjustable band 910 is tightened around the hemorrhoid. The adjustable band 910 may also be fed through a catheter. The catheters may be sized to be fed through the working channels of any of the aforementioned devices to treat hemorrhoids.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather, modifications are also covered within the scope of the present invention as defined by the appended claims.

The invention claimed is:

1. A device, comprising:
an anoscope including an elongated hollow member with a longitudinal slot configured to receive tissue in an interior of the hollow member; and
a clip applicator including a body slidably received in the slot, the clip applicator including jaws at a distal end of the body configured to hold a ligation clip, the clip applicator further including a plunger slidably coupled to the body configured to actuate the jaws, the clip applicator further including rails extending along a longitudinal side of the body, each of the rails being sized and shaped to be inserted through a corresponding channel extending along at least a portion of a longitudinal edge of the slot;
wherein when the clip applicator is inserted into the slot and the plunger is moved relative to the body, the jaws close and deform the ligation clip from an open position into a closed position around tissue received in the slot.

2. The device of claim 1, further comprising:
a notch at a distal end of each of the jaws, each of the notches configured to abut an end of the ligation clip to hold and lock the ligation clip in a configuration; and
a pin at a proximal end of each of the jaws, each of the pins maintaining parallel and simultaneous movement between the jaws.

3. The device of claim 1, further comprising:
a linkage constructed to facilitate movement of the jaws from the open position to the closed position when the plunger is pushed proximally towards the body until the plunger abuts the proximal end of the body.

4. The device of claim 3, wherein the linkage includes a pair of angled slots at a distal end of the plunger, each of the angled slots being sized and shaped to receive a rib extending radially inward from each of the jaws.

5. The device of claim 1, further comprising:
a clip cartridge housing a plurality of ligation bands.

6. The device of claim 1, wherein the jaws are locked in a proximal direction and a distal direction, restricting the jaws to lateral movement, transverse to a longitudinal axis of the clip applicator.

7. The device of claim 1, wherein the anoscope includes a plurality of longitudinal slots configured to receive tissue in the interior of the hollow member.

8. A device, comprising:
an anoscope including an elongated hollow member with a longitudinal slot configured to receive tissue in an interior of the hollow member; and
a clip applicator comprising:
a body slidably received in the slot;
a jaws at a distal end of the body configured to hold a ligation clip;
a plunger slidably coupled to the body configured to actuate the jaws;
a handle portion extending from a proximal end to a distal end;
a thumb ring attached to the proximal end;
a longitudinal slot extending a portion of a length of the handle portion distal to the thumb ring;
a core wire;
a spool disposed around the handle portion, the spool slidable between the proximal end and the distal end of the longitudinal slot; and
a thin flexible coil extending distally from the distal end of the handle portion;
wherein when the clip applicator is inserted into the slot and the plunger is moved relative to the body, the jaws close and deform the ligation clip from an open position into a closed position around tissue received in the slot.

9. The device of claim 8, wherein the spool is a spring-biased with respect to the handle portion.

10. The device of claim 8, wherein the clip applicator further comprises:
a capsule extending from a proximal end to a distal end and housing a yoke slidable therewithin; and
two clip jaws, sized and shaped to grasp tissue, the jaws extending through two holes at the distal end of the capsule, attached to the yoke.

11. The device of claim 8, wherein the clip applicator further comprises a feedback notification notifying a user when the ligation clip is deployed.

12. The device of claim 11, wherein the feedback notification is one of an aural feedback or a tactile feedback.

13. The device of claim 8, wherein the anoscope further comprises a distal tip with a curved surface for insertion into an anal cavity.

14. The device of claim 8, wherein the anoscope includes a plurality of longitudinal slots configured to receive tissue in the interior of the hollow member.

15. A system, comprising:
a dilator sized and shaped for insertion into an anal cavity; and
a device, comprising:
an anoscope including an elongated hollow member with a longitudinal slot configured to receive tissue in an interior of the hollow member; and
a clip applicator including a body slidably received in the slot, the clip applicator including jaws at a distal end of the body configured to hold a ligation clip, the clip applicator further including a plunger slidably coupled to the body configured to actuate the jaws, the clip applicator further including rails extending along a longitudinal side of the body, each of the rails being sized and shaped to be inserted through a corresponding channel extending along at least a portion of a longitudinal edge of the slot,
wherein when the clip applicator is inserted into the slot and the plunger is moved relative to the body, the jaws close and deform the ligation clip from an open position into a closed position around tissue received in the slot; and
wherein the dilator is configured to be inserted into the anal cavity prior to the insertion of the anoscope into the anal cavity.

16. The system of claim 15, wherein the anoscope is insertable into the anal cavity via the dilator.

17. A method, comprising:
inserting an anoscope into an anal cavity, the anoscope including an elongated hollow member with a longitudinal slot for receiving tissue in an interior of the hollow member;
inserting a clip applicator through the slot to engage target tissue, the clip applicator including a body slidably received in the slot, the clip applicator including jaws at a distal end of the body for holding a ligation clip, the clip applicator further including a plunger slidably coupled to the body for actuating the jaws, the clip applicator further including rails extending along a longitudinal side of the body, each of the rails being sized and shaped to be inserted through a corresponding channel extending along at least a portion of a longitudinal edge of the slot; and
moving the plunger relative to the body to close the jaws and deform the ligation clip from an open position into a closed position around a first target portion of tissue received between the jaws.

18. A method, comprising:
inserting an anoscope into an anal cavity, the anoscope including an elongated hollow member with an open distal end for receiving tissue in an interior of the hollow member;
inserting a clip applicator into a first one of channels, the clip applicator including a distal portion slidably received in the first channel, the clip applicator including jaws at a distal end of a body for holding a ligation clip, the clip applicator further including a plunger slidably coupled to the body for actuating the jaws the clip applicator further including a handle portion extending from a proximal end to a distal end, the clip applicator further including a thumb ring attached to the proximal end, the clip applicator further including a longitudinal slot extending a portion of a length of the handle portion distal to the thumb ring, the clip applicator further including a core wire, the clip applicator further including a spool disposed around the handle portion, the spool slidable between the proximal end and the distal end of the longitudinal slot, the clip applicator further including a thin flexible coil extending distally from the distal end of the handle portion; and
moving the plunger relative to the body to close the jaws and deform the ligation clip from an open position into a closed position around a first target portion of tissue received in the open distal end.

19. A system, comprising:
a dilator sized and shaped for insertion into an anal cavity; and
a device, comprising:
an anoscope including an elongated hollow member with a longitudinal slot configured to receive tissue in an interior of the hollow member; and a clip applicator including a body slidably received in the slot, the clip applicator including jaws at a distal end of the body configured to hold a ligation clip, the clip applicator further including a plunger slidably coupled to the body configured to actuate the jaws, the clip applicator further including a handle portion extending from a proximal end to a distal end, the clip applicator further including a thumb ring attached to the proximal end, the clip applicator further including a longitudinal slot extending a portion of a length of the handle portion distal to the thumb ring, the clip applicator further including a core wire, the clip applicator further including a spool disposed around the handle portion, the spool slidable between the proximal end and the distal end of the longitudinal slot, the clip applicator further including a thin flexible coil extending distally from the distal end of the handle portion, wherein when the clip applicator is inserted into the slot and the plunger is moved relative to the body, the jaws close and deform the ligation clip from an open position into a closed position around tissue received in the slot; and wherein the dilator is configured to be inserted into the anal cavity prior to the insertion of the anoscope into the anal cavity.

20. The system of claim 19, wherein the anoscope is insertable into the anal cavity via the dilator.

\* \* \* \* \*